US010381188B2

(12) United States Patent
Hirayama

(10) Patent No.: US 10,381,188 B2
(45) Date of Patent: Aug. 13, 2019

(54) RADIOGRAPHIC IMAGE DIAGNOSTIC APPARATUS AND X-RAY TUBE

(71) Applicant: TOSHIBA MEDICAL SYSTEMS CORPORATION, Otawara-shi (JP)

(72) Inventor: Hiroshi Hirayama, Nasushiobara (JP)

(73) Assignee: Canon Medical Systems Corporation, Otawara-shi (JP)

(*) Notice: Subject to any disclaimer, the term of this patent is extended or adjusted under 35 U.S.C. 154(b) by 345 days.

(21) Appl. No.: 15/299,815

(22) Filed: Oct. 21, 2016

(65) Prior Publication Data

US 2017/0148606 A1    May 25, 2017

(30) Foreign Application Priority Data

Nov. 24, 2015  (JP) .................. 2015-229123

(51) Int. Cl.
| | | |
|---|---|---|
| H01J 35/02 | (2006.01) | |
| A61B 6/03 | (2006.01) | |
| H01J 35/06 | (2006.01) | |
| H01J 35/10 | (2006.01) | |
| A61B 6/06 | (2006.01) | |
| A61B 6/00 | (2006.01) | |
| H01J 35/30 | (2006.01) | |

(52) U.S. Cl.
CPC .......... *H01J 35/025* (2013.01); *A61B 6/032* (2013.01); *A61B 6/06* (2013.01); *A61B 6/4488* (2013.01); *H01J 35/06* (2013.01); *H01J 35/101* (2013.01); *H01J 35/103* (2013.01); *H01J 35/305* (2013.01); *H01J 2235/1026* (2013.01)

(58) Field of Classification Search
None
See application file for complete search history.

(56) References Cited

U.S. PATENT DOCUMENTS 4,081,707 A    3/1978  Hartl et al.
4,769,831 A *  9/1988  Broenner ............ H01J 35/103
                                                  378/125

(Continued)

FOREIGN PATENT DOCUMENTS

| JP | 61-279049 | 12/1986 |
| JP | 4-301399 | 10/1992 |
| JP | 4-355037 | 12/1992 |

(Continued)

OTHER PUBLICATIONS

Japanese Office Action dated Jun. 18, 2019 in Japanese Patent Application No. JP2015-229123.

*Primary Examiner* — Hoon K Song
(74) *Attorney, Agent, or Firm* — Oblon, McClelland, Maier & Neustadt, L.L.P.

(57) ABSTRACT

A radiographic image diagnostic apparatus according to embodiments includes an X-ray tube, a holding member, and coil control circuitry. The X-ray tube includes: a cathode that emits electrons; coils that generate electromagnetic force; and an anode that rotates about a rotation axis in response to the electromagnetic force and to generate an X-ray by receiving the electrons. The holding member holds the X-ray tube so that the X-ray tube is movable. The coil control circuitry controls a current to be supplied to the coils based on at least one of a position of the X-ray tube, a direction of the X-ray tube, or a velocity of the X-ray tube.

13 Claims, 14 Drawing Sheets

(56) References Cited

U.S. PATENT DOCUMENTS 4,780,900 A      10/1988   Gabbay et al.
5,696,804 A  *  12/1997   Ono ...................... A61B 6/032
                                                              378/125

FOREIGN PATENT DOCUMENTS

| JP | 6-70921 | 3/1994 |
| JP | 2006-100032 | 4/2006 |
| JP | 2008-166059 A | 7/2008 |
| JP | 2011-130954 | 7/2011 |

* cited by examiner

FIG.8
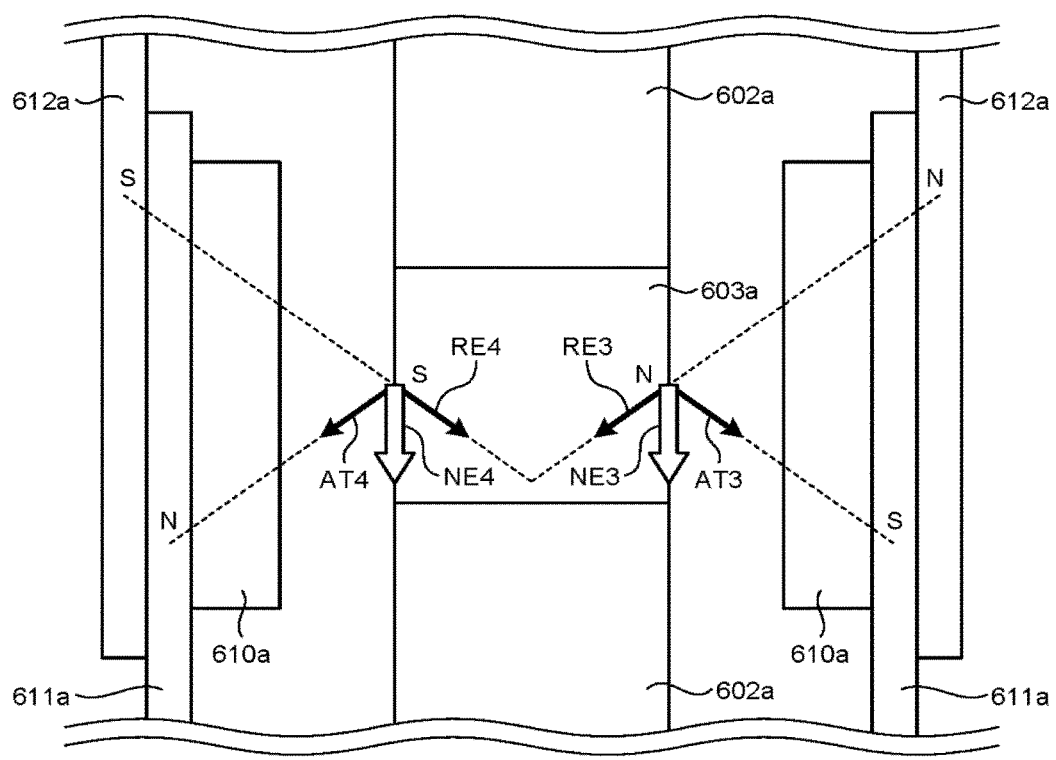
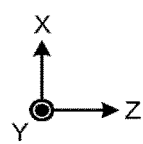

RADIOGRAPHIC IMAGE DIAGNOSTIC APPARATUS AND X-RAY TUBE

CROSS-REFERENCE TO RELATED APPLICATIONS

This application is based upon and claims the benefit of priority from Japanese Patent Application No. 2015-229123, filed on Nov. 24, 2015; the entire contents of which are incorporated herein by reference.

FIELD

Embodiments described herein relate generally to a radiographic image diagnostic apparatus and an X-ray tube.

BACKGROUND

One type of X-ray tube is a rotating anode X-ray tube. The rotating anode X-ray tube is configured to rotate an anode that generates an X-ray and cause electrons to collide with a part of the anode that orbits on a circular orbit around a point on a rotation axis, thereby generating an X-ray. In general, the anode of the rotating anode X-ray tube is supported by bearings.

BRIEF DESCRIPTION OF THE DRAWINGS

FIG. 8 is a diagram for describing attraction and repulsion for rotating the anode about the rotation axis by the X-ray tube according to the first embodiment;

DETAILED DESCRIPTION

A radiographic image diagnostic apparatus according to embodiments described herein includes an X-ray tube, a holding member, and coil control circuitry. The X-ray tube includes: a cathode that emits electrons; a coil that generates electromagnetic force; and an anode that rotates about a rotation axis in response to the electromagnetic force and to generate an X-ray by receiving the electrons. The holding member holds the X-ray tube so that the X-ray tube is movable. The coil control circuitry controls a current to be supplied to the coils based on at least one of a position of the X-ray tube, a direction of the X-ray tube, or a velocity of the X-ray tube.

Referring to the accompanying drawings, a radiographic image diagnostic apparatus and an X-ray tube according to the embodiments are now described. Note that, in the following embodiments, overlapping descriptions are omitted as appropriate.

First Embodiment

Figure 1:
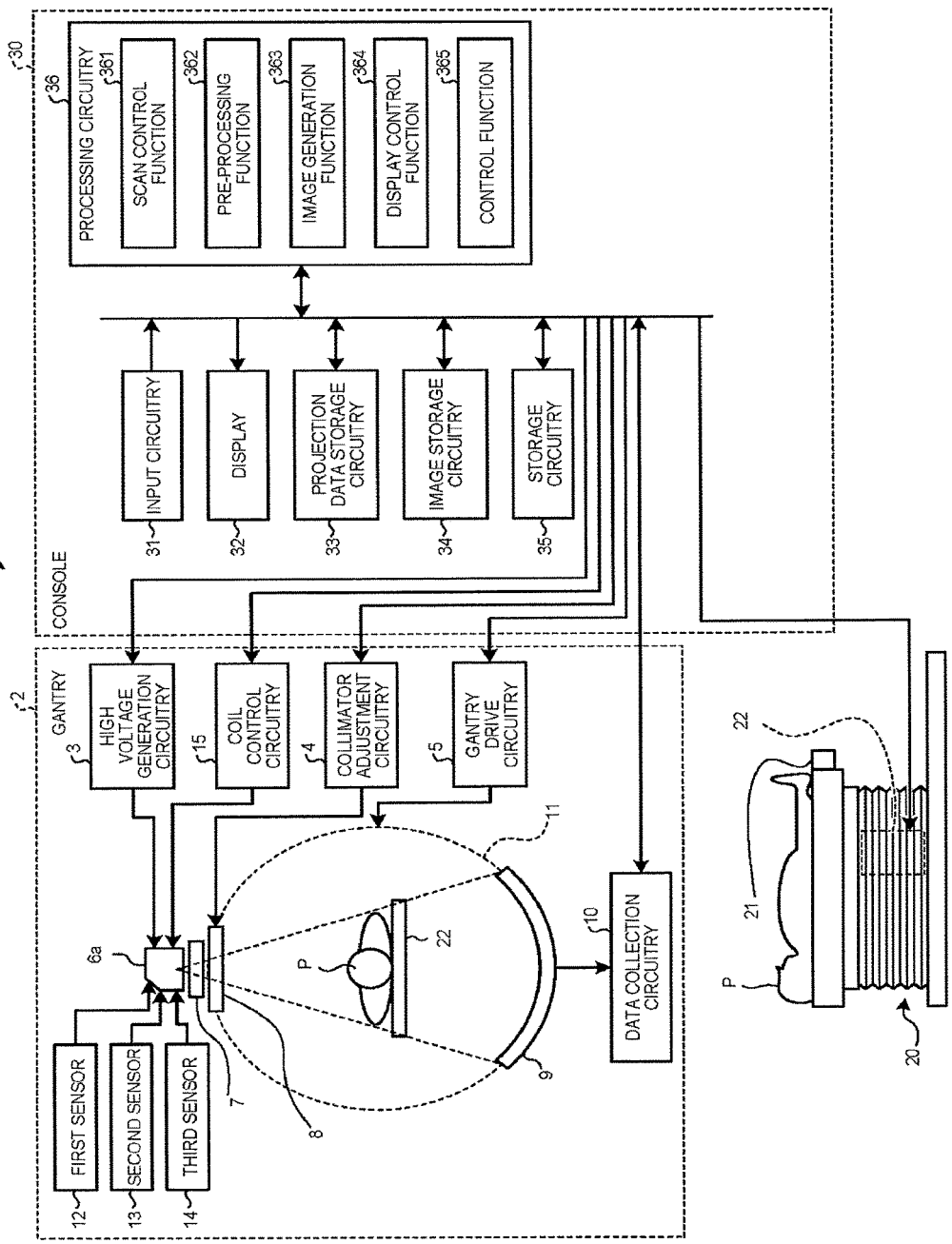
FIG. 1 is a diagram illustrating a configuration example of an X-ray CT apparatus according to a first embodiment.

Referring to FIG. 1, the configuration of an X-ray CT apparatus 1 according to a first embodiment is now described. FIG. 1 is a diagram illustrating a configuration example of the X-ray CT apparatus according to the first embodiment. As illustrated in FIG. 1, the X-ray CT apparatus 1 includes a gantry 2, a couch 20, and a console 30. Note that the X-ray CT apparatus 1 is one type of radiographic image diagnostic apparatus. The configuration of the X-ray CT apparatus 1 is not limited to the following configuration.

The gantry 2 includes high voltage generation circuitry 3, collimator adjustment circuitry 4, gantry drive circuitry 5, an X-ray tube 6a, a wedge 7, a collimator 8, a detector 9, data collection circuitry 10, a rotating frame 11, a first sensor 12, a second sensor 13, a third sensor 14, and coil control circuitry 15.

The high voltage generation circuitry 3 supplies a tube voltage to the X-ray tube 6a. The collimator adjustment circuitry 4 adjusts the aperture and position of the collimator 8 to adjust an irradiation range of an X-ray generated by the X-ray tube 6a. The gantry drive circuitry 5 rotates the rotating frame 11 to turn the X-ray tube 6a and the detector 9 on a circular orbit around a subject P.

The X-ray tube 6a generates an X-ray with the tube voltage supplied from the high voltage generation circuitry 3. Details of the X-ray tube 6a are described later.

The wedge 7 is an X-ray filter for adjusting the dose of the X-ray generated by the X-ray tube 6a. The collimator 8 is a slit for adjusting the irradiation range of the X-ray. The aperture and position of the collimator 8 are adjusted by the collimator adjustment circuitry 4.

The detector 9 detects an X-ray. The detector 9 includes a plurality of detection elements. The detector 9 detects the X-ray generated by the X-ray tube 6a with the detection elements. The detection elements convert the incident X-ray into an electric signal and output the converted electric signal to the data collection circuitry 10. The size, shape, and number of the detection elements included in the detector 9 are not particularly limited. Note that the detector 9 may be either of a direct conversion detector or an indirect conversion detector. The data collection circuitry 10 generates projection data based on the electric signal output from the detection elements.

The rotating frame 11 is an annular frame. The rotating frame 11 supports the X-ray tube 6a and the detector 9. The X-ray tube 6a and the detector 9 are faced each other. The rotating frame 11 is driven by the gantry drive circuitry 5 to rotate about the subject P. The rotating frame 11 is also referred to as "holding member". The holding member holds the above-mentioned X-ray tube so that the X-ray tube is movable. A mechanism for moving the X-ray tube is optionally employed.

The first sensor 12 detects the position of the X-ray tube 6a. For example, the first sensor 12 is mounted to the gantry 2 as illustrated in FIG. 1. Alternatively, the first sensor 12 is mounted to the X-ray tube 6a. A method of detecting the position of the X-ray tube 6a by the first sensor 12 is not particularly limited.

The second sensor 13 detects the direction of the X-ray tube 6a. For example, the second sensor 13 is mounted to the gantry 2 as illustrated in FIG. 1. Alternatively, the second sensor 13 is mounted to the X-ray tube 6a. A method of detecting the direction of the X-ray tube 6a by the second sensor 13 is not particularly limited.

The third sensor 14 detects the velocity of the X-ray tube 6a. For example, the third sensor 14 is mounted to the gantry 2 as illustrated in FIG. 1. Alternatively, the third sensor 14 is mounted to the X-ray tube 6a. A method of detecting the velocity of the X-ray tube 6a by the third sensor 14 is not particularly limited.

The coil control circuitry 15 includes floating coil control circuitry and propulsion coil control circuitry. The floating coil control circuitry controls a current to be supplied to a floating coil 610a based on at least one of the position of the X-ray tube 6a, the direction of the X-ray tube 6a, the velocity of the X-ray tube 6a, or the position of an anode 601a in the X-ray tube 6a. The propulsion coil control circuitry controls currents to be supplied to a propulsion coil 611a and a propulsion coil 612a, thereby controlling the rotation of the anode 601a. Details of the coil control circuitry 15 are described later.

The couch 20 includes a couchtop 21 and couch drive circuitry 22. The couchtop 21 is a plate-shaped member for putting the subject P thereon. The couch drive circuitry 22 moves the couchtop 21 having the subject P put thereon, thereby moving the subject P within an imaging space in the gantry 2.

The console 30 includes input circuitry 31, a display 32, projection data storage circuitry 33, image storage circuitry 34, storage circuitry 35, and processing circuitry 36.

The input circuitry 31 is used by a user to input instructions and settings. For example, the input circuitry 31 is included in a mouse or a keyboard. The input circuitry 31 transfers the instructions and settings input by the user to the processing circuitry 36. For example, the input circuitry 31 is implemented by a processor.

The display 32 is a monitor to be referred to by the user. For example, the display 32 receives, from the processing circuitry 36, an instruction to display a CT image or a graphical user interface (GUI) used for the user to input instructions and settings. The display 32 displays a CT image or a GUI based on the instruction.

The projection data storage circuitry 33 stores therein raw data generated by a pre-processing function 362 described later. The image storage circuitry 34 stores therein CT images generated by an image generation function 363 described later.

The storage circuitry 35 stores therein a computer program used for the high voltage generation circuitry 3, the collimator adjustment circuitry 4, the gantry drive circuitry 5, the data collection circuitry 10, and the coil control circuitry 15 to implement the above-mentioned function. The storage circuitry 35 stores therein a computer program used for the couch drive circuitry 22 to implement the above-mentioned function. The storage circuitry 35 stores therein a computer program used for the processing circuitry 36 to implement each of a scan control function 361, the pre-processing function 362, the image generation function 363, a control function 365, and other functions described later. Therefore, the high voltage generation circuitry 3, the collimator adjustment circuitry 4, the gantry drive circuitry 5, the data collection circuitry 10, the coil control circuitry 15, the couch drive circuitry 22, and the processing circuitry 36 implement their functions by reading and executing the computer programs stored in the storage circuitry 35.

Furthermore, the projection data storage circuitry 33, the image storage circuitry 34, and the storage circuitry 35 each include a storage medium whose stored information is readable by a computer. Examples of the storage medium include a hard disk.

The processing circuitry 36 has the scan control function 361, the pre-processing function 362, the image generation function 363, a display control function 364, and the control function 365. Details of these functions are described later. For example, the processing circuitry 36 is implemented by a processor.

Figure 2:
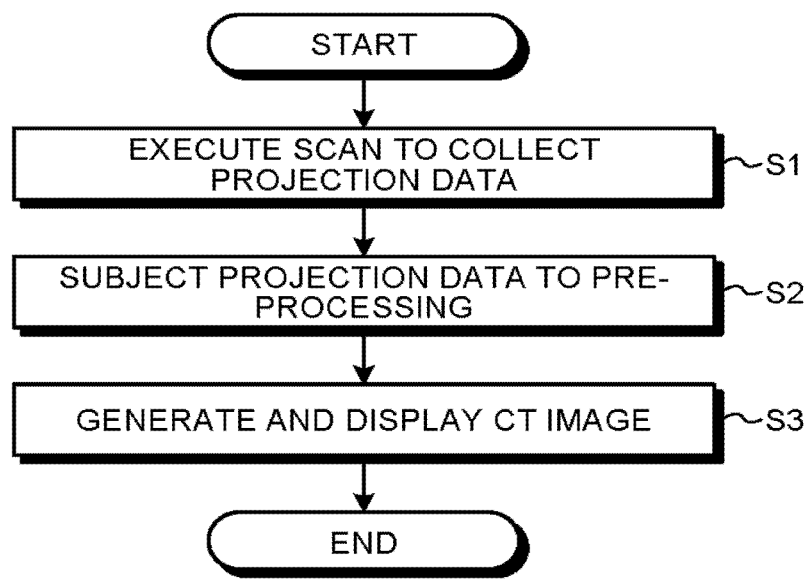
FIG. 2 is a flowchart illustrating an example of processing performed by the X-ray CT apparatus according to the first embodiment.

Referring to FIG. 2, an example of processing of the X-ray CT apparatus 1 according to the first embodiment is now described. FIG. 2 is a flowchart illustrating an example of processing performed by the X-ray CT apparatus according to the first embodiment.

As illustrated in FIG. 2, the processing circuitry 36 executes a scan to collect projection data (Step S1). For example, the processing of Step S1 is as follows.

The processing circuitry 36 reads a computer program corresponding to the scan control function 361 from the storage circuitry 35, and executes the read computer program. The scan control function 361 is a function of controlling the X-ray CT apparatus 1 in order to execute a scan. For example, the processing circuitry 36 executes the scan control function 361 to control the X-ray CT apparatus 1 as follows.

The processing circuitry 36 controls the couch drive circuitry 22 to move the subject P into an imaging space in the gantry 2. The processing circuitry 36 controls the gantry 2 to scan the subject P. Specifically, the processing circuitry 36 controls the high voltage generation circuitry 3 to supply a tube voltage to the X-ray tube 6a. The processing circuitry 36 controls the collimator adjustment circuitry 4 to adjust the aperture and position of the collimator 8. Furthermore, the processing circuitry 36 controls the gantry drive circuitry 5 to rotate the rotating frame 11. Then, the processing circuitry 36 controls the data collection circuitry 10 so that the data collection circuitry 10 collects projection data. Examples of the scan executed by the X-ray CT apparatus 1 include conventional scan, helical scan, and step-and-shoot scan.

As illustrated in FIG. 2, the processing circuitry 36 subjects the projection data to pre-processing (Step S2). For example, the processing of Step S2 is as follows.

The processing circuitry 36 reads a computer program corresponding to the pre-processing function 362 from the storage circuitry 35, and executes the read computer program. The pre-processing function 362 is a function of correcting the projection data generated by the data collection circuitry 10. Examples of the correction include logarithmic transformation, offset correction, sensitivity correction, beam hardening correction, and scatter and attenuation correction. The projection data corrected by the pre-processing function 362 is stored in the projection data storage circuitry 33. Note that the projection data corrected by the pre-processing function 362 is also referred to as "raw data".

As illustrated in FIG. 2, the processing circuitry 36 generates and displays a CT image (Step S3). For example, the processing of Step S3 is as follows.

The processing circuitry 36 reads a computer program corresponding to the image generation function 363 from the storage circuitry 35, and executes the read computer program. The image generation function 363 is a function of reconstructing the raw data stored in the projection data storage circuitry 33 to generate a CT image. Examples of the reconstruction method include inverse projection and iterative reconstruction. The processing circuitry 36 reads a computer program corresponding to the display control function 364 from the storage circuitry 35, and executes the read computer program. The display control function 364 is a function of displaying the CT image stored in the image storage circuitry 34 on the display 32.

Note that the processing circuitry 36 reads a computer program corresponding to the control function 365 from the storage circuitry 35 and executes the read computer program as appropriate in order to execute the above-mentioned processing. The control function 365 includes a function of operating each component of the gantry 2, the couch 20, and the console 30 at timing suited for the purpose, and other functions.

Referring to FIG. 3 to FIG. 8, the structure and operation of the X-ray tube 6a according to the first embodiment are now described. The following description uses the X direction, the Y direction, and the Z direction defined as follows. The direction parallel to a rotation axis Zr of the anode described later is defined as the Z direction. The X direction and the Y direction are orthogonal to the Z direction. The X direction, the Y direction, and the Z direction form a right-handed system. This coordinate system is fixed to the X-ray tube 6a.

Figure 3:
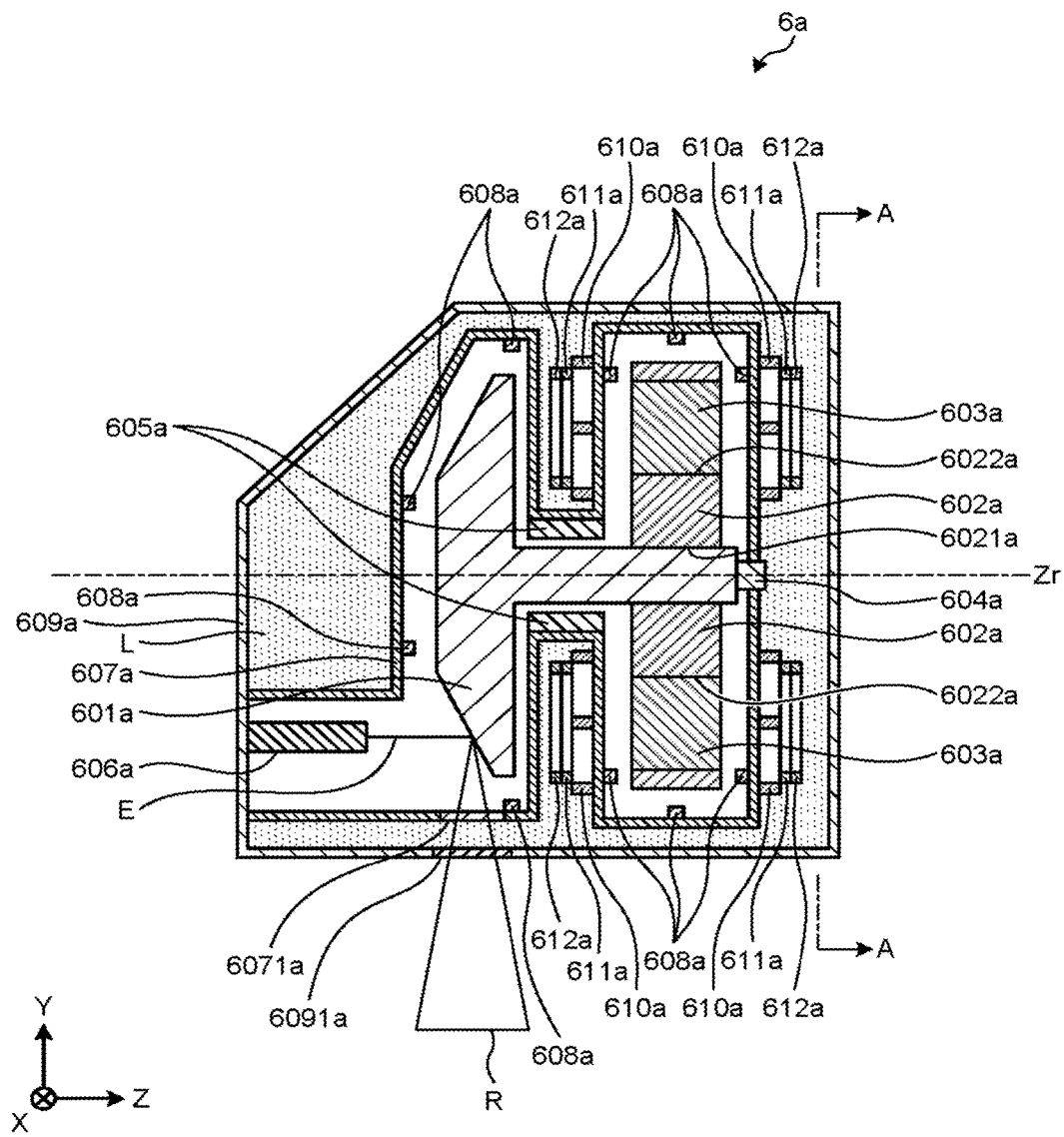
FIG. 3 is a diagram of an X-ray tube according to the first embodiment, which is cut by a plane that passes through a rotation axis Zr and is parallel to the YZ plane, and which is viewed in the −X direction.
Figure 4:
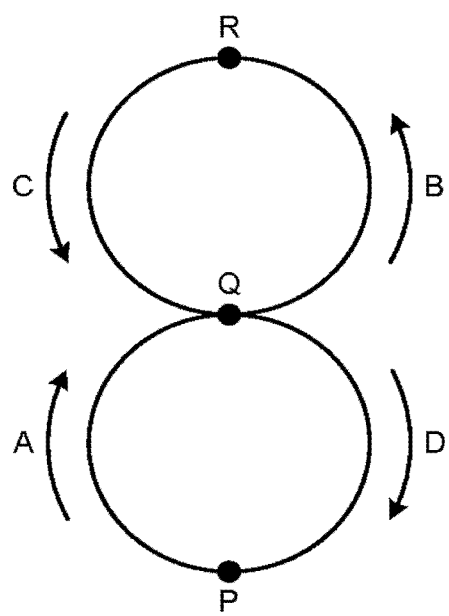
FIG. 4 is a diagram for describing a floating coil according to the first embodiment.
Figure 5:
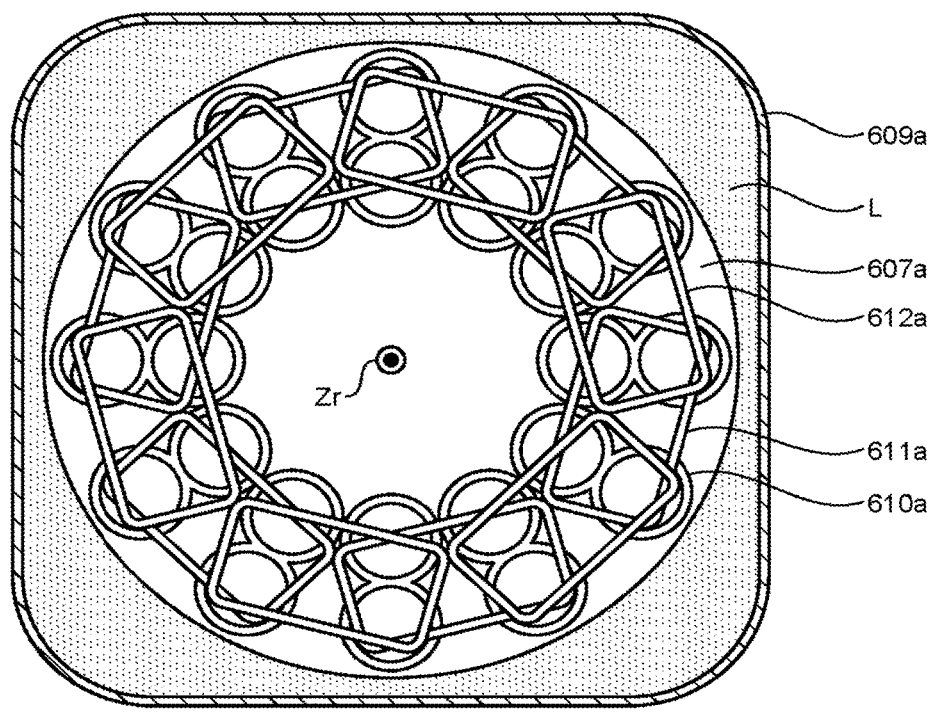
FIG. 5 is a diagram of the X-ray tube according to the first embodiment, which is cut by a plane that passes through the line A-A illustrated in FIG. 3 and is parallel to the XY plane, and which is viewed in the +Z direction.
Figure 6:
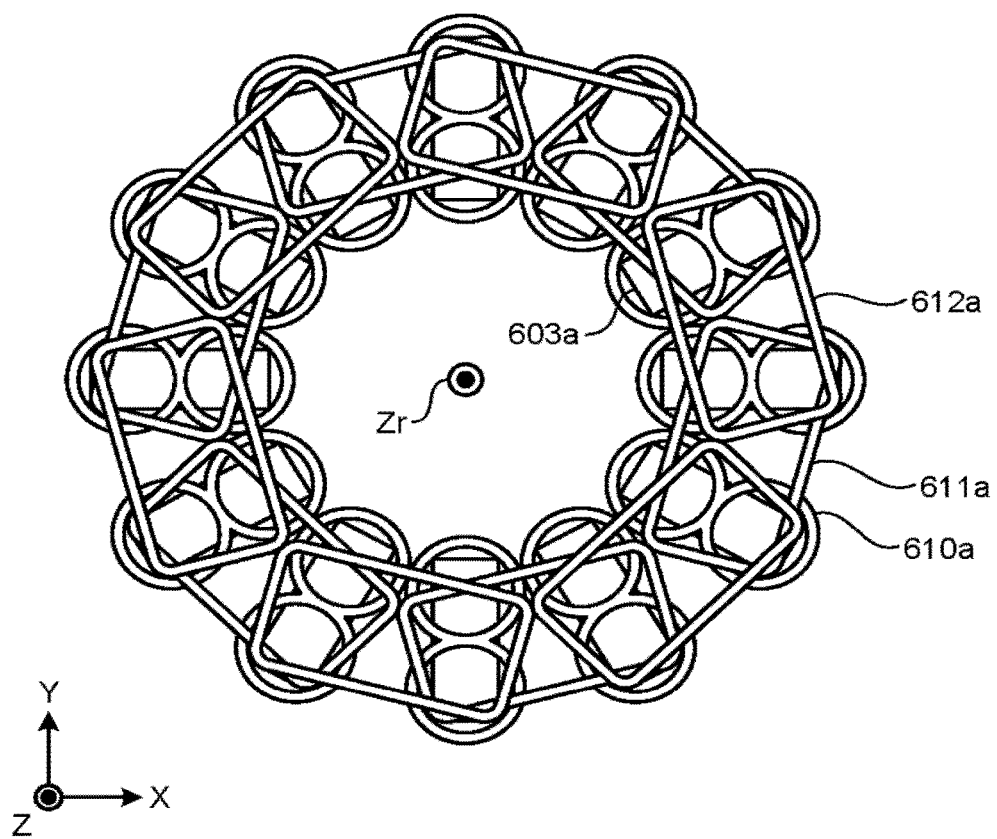
FIG. 6 is a diagram for describing a positional relation among magnets, floating coils, and propulsion coils included in the X-ray tube according to the first embodiment.
Figure 7:
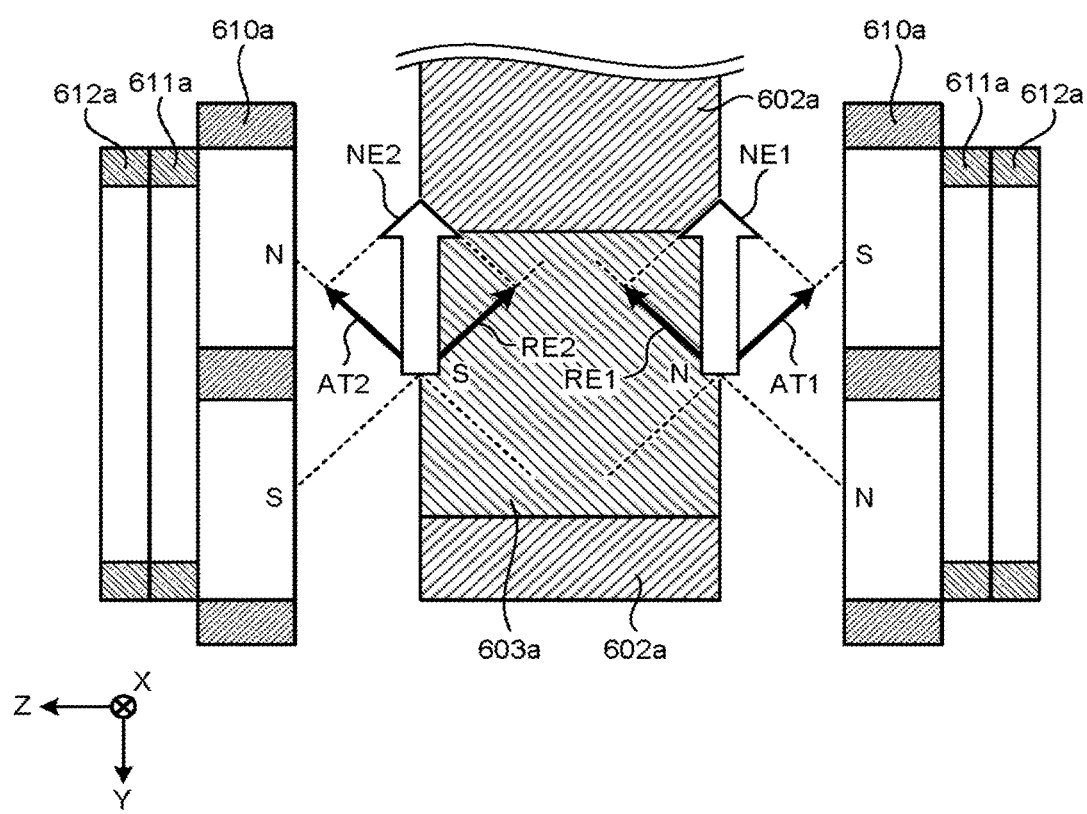
FIG. 7 is a diagram for describing attraction and repulsion for causing an anode to float in the space by the X-ray tube according to the first embodiment.

FIG. 3 is a diagram of the X-ray tube according to the first embodiment, which is cut by a plane that passes through the rotation axis Zr and is parallel to the YZ plane, and which is viewed in the −X direction. FIG. 4 is a diagram for describing the floating coil according to the first embodiment. FIG. 5 is a diagram of the X-ray tube according to the first embodiment, which is cut by a plane that passes through the line A-A illustrated in FIG. 3 and is parallel to the XY plane, and which is viewed in the +Z direction. FIG. 6 is a diagram for describing a positional relation among magnets, the floating coils, and the propulsion coils included in the X-ray tube according to the first embodiment. FIG. 7 is a diagram for describing attraction and repulsion for causing the anode to float in the space by the X-ray tube according to the first embodiment. FIG. 8 is a diagram for describing attraction and repulsion for rotating the anode about the rotation axis by the X-ray tube according to the first embodiment.

As illustrated in FIG. 3, the X-ray tube 6a includes the anode 601a, a heat insulating material 602a, a magnet 603a, a slip ring 604a, a trapping mechanism 605a, a cathode 606a, a first casing 607a, a fourth sensor 608a, a second casing 609a, the floating coil 610a, the propulsion coil 611a, and the propulsion coil 612a. Note that the floating coil 610a, the propulsion coil 611a, and the propulsion coil 612a are sometimes referred to collectively as "coils". The configuration of the X-ray tube 6a is not limited to the following configuration.

As illustrated in FIG. 3, the anode 601a generates an X-ray R by receiving electrons E emitted from the cathode 606a. As illustrated in FIG. 3, the shape of the anode 601a is a solid of revolution about the rotation axis Zr. The anode 601a has a large-radius portion and a small-radius portion. The large-radius portion is located on the −Z direction side of the anode 601a. The small-radius portion is located on the +Z direction side of the anode 601a. The radius as used herein refers to a distance from a line of intersection between a plane perpendicular to the rotation axis Zr and the anode 601a to the rotation axis Zr. The anode 601a receives the electrons E emitted from the cathode 606a at the large-radius portion. As illustrated in FIG. 3, the radius of the portion of the anode 601a at which the electrons E are received becomes smaller as the distance to the cathode 606a becomes smaller.

Furthermore, the anode 601a rotates about the rotation axis Zr while floating in the space due to electromagnetic force. Specifically, the anode 601a floats in the space due to electromagnetic force generated between the floating coil 610a and the magnet 603a. Furthermore, the anode 601a rotates about the rotation axis Zr due to electromagnetic force generated between the propulsion coil 611a and the magnet 603a and electromagnetic force generated between the propulsion coil 612a and the magnet 603a. Accordingly, the portion of the anode 601a at which the electrons E are received orbits on a circular orbit around a point on the rotation axis Zr. Furthermore, the anode 601a generates heat when receiving the electrons E. Note that the anode 601a is grounded.

The heat insulating material 602a prevents heat generated by the anode 601a from being transferred to the magnet 603a. This prevents the strength of magnetic poles generated by the magnet 603a from decreasing. The shape of the heat insulating material 602a is a disc. As illustrated in FIG. 3, the heat insulating material 602a has a hole 6021a and a hole 6022a. Part of the small-radius portion of the anode 601a is inserted in the hole 6021a. The magnet 603a is inserted in the hole 6022a.

The magnet 603a generates magnetic poles. Specifically, the magnet 603a generates a magnetic moment. The magnetic moment generated by the magnet 603a is parallel to the rotation axis Zr. For example, the magnet 603a is a permanent magnet or an electromagnet. An electromagnet to be used may have no core. However, an X-ray tube 6a including a permanent magnet has a configuration simpler than that of an X-ray tube 6a including an electromagnet. The reason is that a permanent magnet needs no wiring or power supply for supplying current.

The magnet 603a is connected to the anode 601a. Specifically, the magnet 603a is inserted into the hole 6022a of the heat insulating material 602a. As illustrated in FIG. 6, the magnets 603a are disposed so as to surround the rotation axis Zr. The magnets 603a orbit on a circular orbit around a point on the rotation axis Zr due to the rotation of the anode 601a. The magnet 603a is influenced by the electromagnetic force generated from the floating coil 610a, the propulsion coil 611a, and the propulsion coil 612a.

The slip ring 604a electrically connects the anode 601a and the cathode 606a to each other. Specifically, the slip ring 604a forms a single closed circuit by electrically connecting the anode 601a and the cathode 606a to each other. In this manner, a potential difference is provided between the anode 601a and the cathode 606a. When the potential difference is large, the electrons E emitted from the cathode 606a fly toward the anode 601a in the direction substantially parallel to the Z direction as illustrated in FIG. 3.

Furthermore, the anode 601a generates heat when receiving the electrons E as described above. It is therefore preferred that the slip ring 604a be made of a heat resistant material. Furthermore, the anode 601a rotates about the rotation axis Zr due to at least one of attraction or repulsion generated between the propulsion coil 611a and the magnet 603a and between the propulsion coil 612a and the magnet 603a. It is therefore preferred that the slip ring 604a have a friction resistant structure. Examples of the friction resistant structure include a fiber brush.

The trapping mechanism 605a traps the anode 601a. Specifically, the trapping mechanism 605a traps the small-radius portion of the rotating anode 601a, for example, in instantaneous power failure, at the power-on of the X-ray tube 6a, or at the power-off of the X-ray tube 6a. The structure of the trapping mechanism 605a is not particularly limited as long as the structure can trap and release the rotating anode 601a. It is preferred that the trapping mechanism 605a be structured not to hinder the rotation of the anode 601a. For example, the trapping mechanism 605a includes balls or parallel rollers at portions that come into contact with the anode 601a. This structure enables the trapping mechanism 605a to keep trapping the anode 601a without hindering the rotation of the anode 601a. Furthermore, for example, the trapping mechanism 605a traps the anode 601a when the X-ray tube 6a is conveyed. The trapping mechanism 605a operates with, for example, power supplied from a dedicated power source or a capacitor for instantaneous power failure.

As illustrated in FIG. 3, the cathode 606a emits the electrons E. For example, the cathode 606a is a filament made of tungsten. A filament emits thermal electrons. Thermal electrons are electrons that are excited by heat generated by a current flowing through the filament and fly out of the filament. The electrons E emitted from the cathode 606a are accelerated by a voltage applied between the anode 601a and the cathode 606a and collide with the anode 601a.

As illustrated in FIG. 3, the first casing 607a houses therein the anode 601a, the heat insulating material 602a, the magnet 603a, the trapping mechanism 605a, the cathode 606a, and the fourth sensor 608a. For example, the first casing 607a is made of glass. Furthermore, the first casing 607a includes a first X-ray window 6071a. The first X-ray window 6071a allows the X-ray R generated by the anode 601a to transmit therethrough. Note that the first casing 607a is also referred to as "insert".

The fourth sensor 608a detects the position of the anode 601a in the X-ray tube 6a. Specifically, the fourth sensor 608a detects the positions of the anode 601a in the X-ray tube 6a in the X direction, the Y direction, and the Z direction. As illustrated in FIG. 3, a plurality of the fourth sensors 608a is mounted to an inner wall of the first casing 607a. Detection results of the fourth sensors 608a are transmitted to the floating coil control circuitry. Note that a method of detecting the positions of the anode 601a in the X direction, the Y direction, and the Z direction by the fourth sensors 608a is not particularly limited.

As illustrated in FIG. 3, the second casing 609a houses therein the first casing 607a, the floating coil 610a, the propulsion coil 611a, and the propulsion coil 612a. The second casing 609a is made of a material that can block the X-ray R generated by the anode 601a. Examples of the material that can block the X-ray R include lead. Furthermore, the second casing 609a includes a second X-ray window 6091a. The second X-ray window 6091a allows the X-ray R generated by the anode 601a to transmit therethrough. Note that the second casing 609a is also referred to as "housing".

As illustrated in FIG. 3, the floating coil 610a is installed between the first casing 607a and the second casing 609a. As illustrated in FIG. 3, the floating coils 610a are disposed so as to be faced each other across the first casing 607a, the magnet 603a, and the heat insulating material 602a. Furthermore, as illustrated in FIG. 5 and FIG. 6, the floating coils 610a are disposed so as to surround the rotation axis Zr. The floating coil 610a does not come into contact with the anode 601a.

The floating coil 610a is formed by winding a conductive wire into a figure of eight. Specifically, the floating coil 610a is manufactured as follows. First, one end of the conductive wire is fixed at the point P illustrated in FIG. 4, and the conductive wire is wound along the arrow A from the point P to the point Q. The conductive wire is wound along the arrow B from the point Q to the point R. The conductive wire is wound along the arrow C from the point R to the point Q. The conductive wire is wound along the arrow D from the point Q to the point P. In other words, the floating coil 610a is manufactured by repeatedly winding a conductive wire in the order of arrow A, arrow B, arrow C, and arrow D.

The floating coil 610a is formed by winding a conductive wire into a figure of eight. Specifically, the floating coil 610a is manufactured as follows. First, one end of the conductive wire is fixed at the point Q illustrated in FIG. 4. Next, the work of winding the conductive wire along the arrow D from the point Q to the point P and winding the conductive wire along the arrow A from the point P to the point Q is repeated. Then, the work of winding the conductive wire along the arrow B from the point Q to the point R and winding the conductive wire along the arrow C from the point R to the point Q is repeated. In other words, the floating coil 610a is manufactured by repeatedly winding a conductive wire in the order of arrow A and arrow D and then repeatedly winding the conductive wire in the order of arrow B and arrow C.

Note that the floating coil 610a may be formed into a shape including two simple closed curves that come into contact with each other at the point Q illustrated in FIG. 4. The simple closed curve as used herein refers to a closed curve that does not intersect with itself. One end of the conductive wire is fixed at any position on the simple closed curves.

The floating coil 610a generates magnetic poles when supplied with current. Specifically, the floating coil 610a generates a magnetic moment when supplied with current. The magnetic moment generated by the floating coil 610a is parallel to the rotation axis Zr. The reason is that the floating coil 610a is disposed so that the coil face thereof is orthogonal to the rotation axis Zr as illustrated in FIG. 3, FIG. 5, and FIG. 6. Note that the magnetic moment refers to a vector quantity obtained by multiplying a vector starting from the S pole and ending at the N pole by the strengths of the magnetic poles of the S pole and the N pole.

One of the magnetic poles of the magnetic moment generated by the floating coil 610a generates at least one of attraction or repulsion between the floating coil 610a and the magnet 603a. This electromagnetic force causes the anode 601a to float in the space. In other words, the floating coil 610a generates at least one of attraction or repulsion between the floating coil 610a and the magnet 603a as the electromagnetic force for causing the anode 601a to float in the space.

Referring to FIG. 7, the method of causing the anode 601a to float in the space by the floating coil 610a is now specifically described. The following description takes the case where the X-ray tube 6a is located on the lowermost side in the gantry 2 as an example. In this case, the X-ray tube 6a generates an X-ray directly upward.

The magnet 603a illustrated in FIG. 7 corresponds to the magnet 603a that is located on the +Y direction side of the rotation axis Zr in FIG. 6. The floating coil 610a, the propulsion coil 611a, and the propulsion coil 612a illustrated in FIG. 7 correspond to the floating coil 610a, the propulsion coil 611a, and the propulsion coil 612a that overlap with the magnet 603a that is located on the +Y direction side of the rotation axis Zr as illustrated in FIG. 6. FIG. 7 illustrates electromagnetic force generated between the magnet 603a and the floating coil 610a when the X-ray tube 6a is located on the lowermost side in the gantry 2.

When the X-ray tube 6a is located on the lowermost side in the gantry 2, gravitational force acting in the +Y direction and centrifugal force acting in the +Y direction act on the anode 601a. It is therefore necessary for the X-ray tube 6a to cause force for cancelling out the gravitational force and the centrifugal force to act on the anode 601a in order to cause the anode 601a to float in the space.

As illustrated in FIG. 7, the floating coil 610a is disposed on each of the +Z direction side and the −Z direction side of the magnet 603a and the heat insulating material 602a. The magnetic poles generated toward the magnet 603a by the floating coil 610a located on the +Z direction side are the S pole on the +Y direction side and the N pole on the −Y direction side. The magnetic poles generated toward the magnet 603a by the floating coil 610a located on the −Z direction side are the N pole on the +Y direction side and the S pole on the −Y direction side. The magnetic pole generated by the magnet 603a toward the floating coil 610a located on the +Z direction side is the S pole. The magnetic pole generated by the magnet 603a toward the floating coil 610a located on the −Z direction side is the N pole.

The S pole generated by the floating coil 610a located on the −Z direction side generates attraction AT1 between this S pole and the N pole generated by the magnet 603a. The N pole generated by the floating coil 610a located on the −Z direction side generates repulsion RE1 between this N pole and the N pole generated by the magnet 603a. Net force NE1 of the attraction AT1 and the repulsion RE1 is force acting in the −Y direction.

The N pole generated by the floating coil 610a located on the +Z direction side generates attraction AT2 between this N pole and the S pole generated by the magnet 603a. The S pole generated by the floating coil 610a located on the +Z direction generates repulsion RE2 between this S pole and the S pole generated by the magnet 603a. Net force NE2 of the attraction AT2 and the repulsion RE2 is force acting in the −Y direction.

When the X-ray tube 6a is located on the lowermost side in the gantry 2, the gravitational force and the centrifugal force acting on the anode 601a are canceled out by the net force NE1 and the net force NE2. Consequently, the X-ray tube 6a can cause the anode 601a to float in the space.

In the above description, the case where the electromagnetic force generated between the magnet 603a, which is located on the +Y direction side of the rotation axis Zr in FIG. 6, and the floating coil 610a, which overlaps with the magnet 603a, causes the anode 601a to float in the space is described, but the embodiments are not limited thereto. Electromagnetic force generated between a magnet 603a other than the magnet 603a that is located on the +Y direction side of the rotation axis Zr in FIG. 6 and the floating coil 610a that overlaps with the magnet 603a may cause the anode 601a to float in the space. In any case, the net force of the electromagnetic force generated between the magnet 603a and the floating coil 610a overlapping with the magnet 603a cancels out the gravitational force and the centrifugal force acting on the anode 601a.

Furthermore, the net force of the electromagnetic force generated between the magnet 603a and the floating coil 610a overlapping with the magnet 603a cancels out the gravitational force and the centrifugal force acting on the anode 601a irrespective of the position of the X-ray tube 6a, the direction of the X-ray tube 6a, and the velocity of the X-ray tube 6a. The floating coil control circuitry controls a current to be supplied to the floating coil 610a based on the position of the X-ray tube 6a, the direction of the X-ray tube 6a, and the velocity of the X-ray tube 6a in order to continuously generate such electromagnetic force.

In addition, the net force of the electromagnetic force generated between the magnet 603a and the floating coil 610a overlapping with the magnet 603a can adjust the position of the anode 601a in the X-ray tube 6a. The adjustment of the position of the anode 601a in the X-ray tube 6a includes controlling the anode 601a to continuously float in the space. Furthermore, the adjustment of the position of the anode 601a in the X-ray tube 6a includes maintaining the state in which the position of the anode 601a in the X-ray tube 6a falls within a predetermined range.

The position of the anode 601a in the X-ray tube 6a is detected by the fourth sensor 608a. The detection result of the fourth sensor 608a is transmitted to the floating coil control circuitry. The floating coil control circuitry controls the current to be supplied to the floating coil 610a based on the detection result of the fourth sensor 608a. In this manner, the floating coil control circuitry can adjust the position of the anode 601a in the X-ray tube 6a.

Note that the floating coil control circuitry may control the current to be supplied to the floating coil 610a based on at least one of the position of the X-ray tube 6a, the direction of the X-ray tube 6a, the velocity of the X-ray tube 6a, or the position of the anode 601a in the X-ray tube 6a. Specifically, the floating coil control circuitry controls the current to be supplied to the floating coil 610a based on a detection result of at least one of the first sensor 12, the second sensor 13, the third sensor 14, or the fourth sensor 608a.

In this manner, the floating coil control circuitry can control the anode 601a to constantly float in the space irrespective of the position of the X-ray tube 6a, the direction of the X-ray tube 6a, the velocity of the X-ray tube 6a, and the position of the anode 601a in the X-ray tube 6a. Furthermore, the floating coil control circuitry can maintain the state in which the position of the anode 601a in the X-ray tube 6a falls within a predetermined range irrespective of the position of the X-ray tube 6a, the direction of the X-ray tube 6a, the velocity of the X-ray tube 6a, and the position of the anode 601a in the X-ray tube 6a.

As illustrated in FIG. 3, the propulsion coil 611a and the propulsion coil 612a are installed between the first casing 607a and the second casing 609a. As illustrated in FIG. 3, the propulsion coils 611a are disposed so as to be faced each other across the first casing 607a, the magnet 603a, the heat insulating material 602a, and the floating coil 610a. As illustrated in FIG. 3, the propulsion coils 612a are disposed so as to be faced each other across the first casing 607a, the magnet 603a, the heat insulating material 602a, the floating coil 610a, and the propulsion coil 611a. Furthermore, as illustrated in FIG. 5 and FIG. 6, the propulsion coils 611a and the propulsion coils 612a are disposed so as to surround the rotation axis Zr. As illustrated in FIG. 5 and FIG. 6, the propulsion coil 611a and the propulsion coil 612a are each formed by winding a conductive wire into a rectangular shape having four rounded corners. The propulsion coil 611a and the propulsion coil 612a do not come into contact with the anode 601a.

The propulsion coil 611a and the propulsion coil 612a generate magnetic poles when supplied with currents. Specifically, the propulsion coil 611a and the propulsion coil 612a generate magnetic moments when supplied with currents. The magnetic moments generated by the propulsion coil 611a and the propulsion coil 612a are parallel to the rotation axis Zr. The reason is that the propulsion coil 611a and the propulsion coil 612a are disposed so that the coil faces thereof are orthogonal to the rotation axis Zr as illustrated in FIG. 3, FIG. 5, and FIG. 6.

One of the magnetic poles of the magnetic moment generated by the propulsion coil 611a generates at least one of attraction or repulsion between the propulsion coil 611a and the magnet 603a. One of the magnetic poles of the magnetic moment generated by the propulsion coil 612a generates at least one of attraction or repulsion between the propulsion coil 612a and the magnet 603a. The electromagnetic force rotates the anode 601a about the rotation axis Zr. Specifically, the propulsion coil 611a and the propulsion coil 612a generate at least one of attraction or repulsion between the propulsion coil 611a and the magnet 603a and between the propulsion coil 612a and the magnet 603a as the electromagnetic force for rotating the anode 601a about the rotation axis Zr.

Referring to FIG. 8, the method of rotating the anode 601a by the propulsion coil 611a and the propulsion coil 612a is specifically described.

FIG. 8 is a diagram of the magnet 603a, the floating coil 610a, the propulsion coil 611a, and the propulsion coil 612a when viewed in the +Y direction. The magnet 603a illustrated in FIG. 8 corresponds to the magnet 603a located at the position in the +Y direction when viewed from the rotation axis Zr in FIG. 6. The floating coil 610a, the propulsion coil 611a, and the propulsion coil 612a illustrated in FIG. 7 correspond to the floating coil 610a, the propulsion coil 611a, and the propulsion coil 612a that overlap with the magnet 603a located at the position in the +Y direction when viewed from the rotation axis Zr in FIG. 6.

As illustrated in FIG. 8, the propulsion coil 611a is disposed on each of the +Z direction side and the −Z direction side of the magnet 603a, the heat insulating material 602a, and the floating coil 610a. The magnetic pole generated toward the magnet 603a by the propulsion coil 611a disposed on the +Z direction side is the S pole. The magnetic pole generated toward the magnet 603a by the propulsion coil 611a disposed on the −Z direction side is the N pole.

As illustrated in FIG. 8, the propulsion coil 612a is disposed on each of the +Z direction side and the −Z direction side of the magnet 603a, the heat insulating material 602a, the floating coil 610a, and the propulsion coil 611a. The magnetic pole generated toward the magnet 603a by the propulsion coil 612a disposed on the +Z direction side is the N pole. The magnetic pole generated toward the magnet 603a by the propulsion coil 612a disposed on the −Z direction side is the S pole.

The magnetic pole generated by the magnet 603a toward the propulsion coil 611a and the propulsion coil 612a disposed on the +Z direction side is the N pole. The magnetic pole generated by the magnet 603a toward the propulsion coil 611a and the propulsion coil 612a disposed on the −Z direction side is the S pole.

The S pole generated by the propulsion coil 611a disposed on the +Z direction side generates attraction AT3 between this S pole and the N pole that is generated by the magnet 603a. The N pole generated by the propulsion coil 612a disposed on the +Z direction side generates repulsion RE3 between this N pole and the N pole that is generated by the magnet 603a. A net force NE3 of the attraction AT3 and the repulsion RE3 is a force acting in the −X direction.

The N pole generated by the propulsion coil 611a disposed on the −Z direction side generates attraction AT4 between this N pole and the S pole that is generated by the magnet 603a. The S pole generated by the propulsion coil 612a disposed on the −Z direction side generates repulsion RE4 between this S pole and the S pole that is generated by the magnet 603a. A net force NE4 of the attraction AT4 and the repulsion RE4 is a force acting in the −X direction.

The net force NE3 and the net force NE4 rotate the anode 601a in a direction in which a right-handed screw rotates when advancing in the +Z direction. Furthermore, the net force of the electromagnetic force generated between the magnet 603a and the propulsion coil 611a overlapping with the magnet 603a and the electromagnetic force generated between the magnet 603a and the propulsion coil 612a overlapping with the magnet 603a also rotates the anode 601a in the direction in which a right-handed screw rotates when advancing in the +Z direction.

For increasing the rotational velocity of the anode 601a, the propulsion coil 611a and the propulsion coil 612a are supplied with current so as to generate the above-mentioned electromagnetic force. For decreasing the rotational velocity of the anode 601a, on the other hand, the propulsion coil 611a and the propulsion coil 612a are supplied with current so as to generate electromagnetic force in the direction opposite to that of the above-mentioned electromagnetic force.

The region between the first casing 607a and the second casing 609a is filled with cooling oil L as illustrated in FIG. 3. The cooling oil L absorbs heat generated by the anode 601a through heat radiation. Consequently, the cooling oil L can prevent the heat generated by the anode 601a from being transferred to other parts of the X-ray tube 6a. Furthermore, the cooling oil L can cool the floating coil 610a, the propulsion coil 611a, and the propulsion coil 612a through heat conduction.

In addition, the cooling oil L is circulated by a pump connected to the region between the first casing 607a and the second casing 609a. Consequently, the above-mentioned effect of the cooling oil L is further enhanced. Note that the pump is installed in a region other than the region between the first casing 607a and the second casing 609a.

As described above, the X-ray CT apparatus 1 according to the first embodiment includes the X-ray tube 6a. The X-ray tube 6*a* causes the anode 601*a* to float in the space by electromagnetic force, and hence does not require a bearing whose central axis is the rotation axis Zr and which is disposed between the anode 601*a* and the first casing 607*a*.

Consequently, the X-ray tube 6*a* can improve the rotational velocity of the anode 601*a*. This enables the X-ray tube 6*a* to reduce the area of the portion of the anode 601*a* at which the electrons E are received. Furthermore, the X-ray tube 6*a* can suppress operational noise. In addition, no risk arises in that the X-ray tube 6*a* cannot be used because bearings are deteriorated due to friction.

In addition to the advantage in that the X-ray tube 6*a* requires no bearing, the floating coil 610*a*, the propulsion coil 611*a*, and the propulsion coil 612*a* are disposed so that the coil faces thereof are orthogonal to the rotation axis Zr. This arrangement reduces the radial dimension of the X-ray tube 6*a* about the rotation axis Zr. The X-ray tube 6*a* is therefore suited for the X-ray CT apparatus 1, which is required to be small in radial dimension.

The X-ray tube 6*a* includes the floating coil control circuitry. The floating coil control circuitry controls the current to be supplied to the floating coil 610*a* based on at least one of the position of the X-ray tube 6*a*, the direction of the X-ray tube 6*a*, the velocity of the X-ray tube 6*a*, or the position of the anode 601*a* in the X-ray tube 6*a*. Consequently, the floating coil control circuitry can cause the anode 601*a* to continuously float in the space. Therefore, the X-ray CT apparatus 1 can obtain the above-mentioned effects irrespective of the position of the X-ray tube 6*a* in the gantry 2.

In addition, the X-ray tube 6*a* can adjust the position of the anode 601*a* in the X-ray tube 6*a* by the floating coil 610*a*. Consequently, the X-ray tube 6*a* can prevent the portion of the anode 601*a* at which the electrons E are received from being displaced due to thermal expansion of the anode 601*a*. Furthermore, as described above, the X-ray tube 6*a* can reduce the area of the portion of the anode 601*a* at which the electrons E are received. Consequently, the X-ray tube 6*a* can stably generate the X-ray R. Therefore, the X-ray CT apparatus 1 according to the first embodiment can generate a high-definition CT image.

The gantry 2 may include no first sensor 12. In this case, for example, the gantry 2 calculates the position of the X-ray tube based on the position of the X-ray tube at the start of scan and the velocity of the X-ray tube during the scan.

The gantry 2 may include no second sensor 13. In this case, for example, the gantry 2 specifies the direction of the X-ray tube based on the position of the X-ray tube.

The gantry 2 may include no third sensor 14. In this case, for example, the gantry 2 calculates the velocity of the X-ray tube based on the position of the X-ray tube at the start of scan and the time elapsed from the start of scan.

The floating coil 610*a* may include a first coil and a second coil that are each formed by winding a conductive wire into a circle. In this case, the direction of current that flows through the first coil and the direction of current that flows through the second coil are opposite to each other. In this manner, the arrangement of magnetic poles described above with reference to FIG. 7 is achieved.

At least one of the floating coil 610*a*, the propulsion coil 611*a*, or the propulsion coil 612*a* may be disposed on the inner side of the first casing 607*a*. Note that it is easier for users to perform repair and maintenance of the X-ray tube 6*a* when the floating coil 610*a*, the propulsion coil 611*a*, and the propulsion coil 612*a* are disposed on the outer side of the first casing 607*a*.

At least one of the floating coil 610*a*, the propulsion coil 611*a*, or the propulsion coil 612*a* may be disposed on the outer side of the second casing 609*a*. In this case, the floating coil 610*a*, the propulsion coil 611*a*, and the propulsion coil 612*a* that are disposed on the outer side of the second casing 609*a* do not come into contact with the cooling oil L. The cooling oil L, however, can absorb heat generated by the floating coil 610*a*, the propulsion coil 611*a*, and the propulsion coil 612*a* that are disposed on the outer side of the second casing 609*a* with the second casing 609*a* interposed between the coils and the cooling oil L. Consequently, the cooling oil L can cool the floating coil 610*a*, the propulsion coil 611*a*, and the propulsion coil 612*a* disposed on the outer side of the second casing 609*a*.

Second Embodiment

In the first embodiment, the anode 601*a*, the heat insulating material 602*a*, and the magnet 603*a* are away from the first casing 607*a*. In a second embodiment, on the other hand, an anode 601*b*, a heat insulating material 602*b*, and a magnet 603*b* are connected to a first casing 607*b*. An X-ray tube 6*b* according to the second embodiment is now described. Note that the contents overlapping with those in the first embodiment are denoted by the same reference symbols and detailed descriptions thereof are omitted.

The first sensor 12 detects the position of the X-ray tube 6*b*. For example, the first sensor 12 is mounted to the gantry 2. Alternatively, the first sensor 12 is mounted to the X-ray tube 6*b*. A method of detecting the position of the X-ray tube 6*b* by the first sensor 12 is not particularly limited.

The second sensor 13 detects the direction of the X-ray tube 6*b*. For example, the second sensor 13 is mounted to the X-ray tube 6*b*. A method of detecting the direction of the X-ray tube 6*b* by the second sensor 13 is not particularly limited.

The third sensor 14 detects the velocity of the X-ray tube 6*b*. For example, the third sensor 14 is mounted to the gantry 2. Alternatively, the third sensor 14 is mounted to the X-ray tube 6*b*. A method of detecting the velocity of the X-ray tube 6*b* by the third sensor 14 is not particularly limited.

Figure 9:
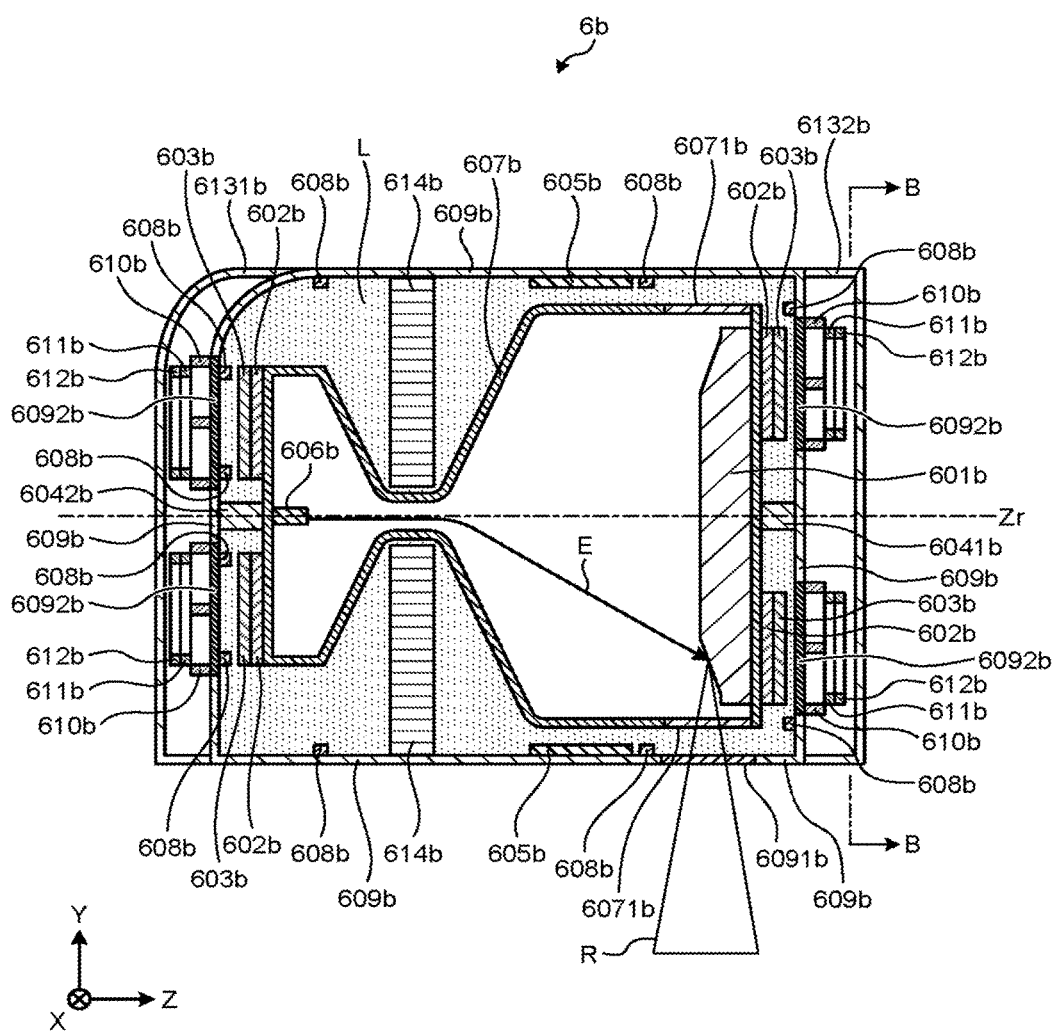
FIG. 9 is a diagram of an X-ray tube according to a second embodiment, which is cut by a plane that passes through a rotation axis Zr and is parallel to the YZ plane, and which is viewed in the −X direction.
Figure 10:
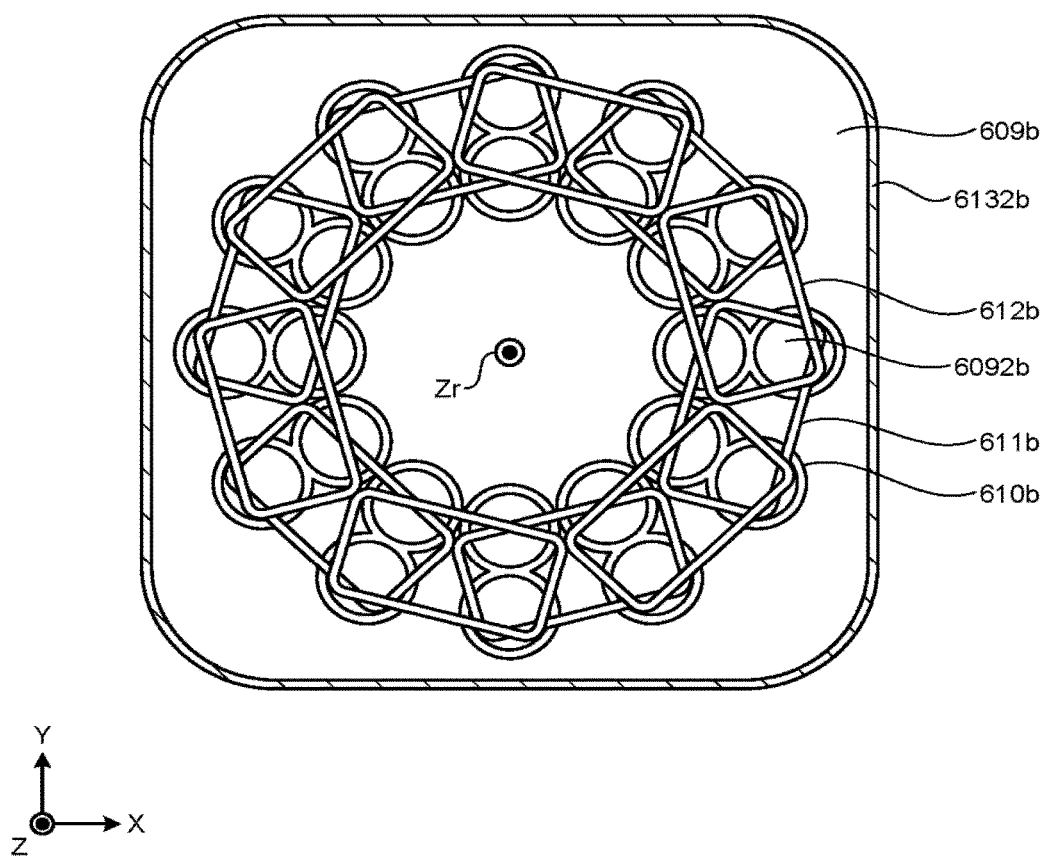
FIG. 10 is a diagram of the X-ray tube according to the second embodiment, which is cut by a plane that passes through the line B-B illustrated in FIG. 9 and is parallel to the XY plane, and which is viewed in the +Z direction.

Referring to FIG. 9 and FIG. 10, the structure and behavior of the X-ray tube 6*b* according to the second embodiment are described. FIG. 9 is a diagram of the X-ray tube according to the second embodiment, which is cut by a plane that passes through the rotation axis Zr and is parallel to the YZ plane, and which is viewed in the −X direction. FIG. 10 is a diagram of the X-ray tube according to the second embodiment, which is cut by a plane that passes through the line B-B illustrated in FIG. 9 and is parallel to the XY plane, and which is viewed in the +Z direction. An X-ray CT apparatus according to the second embodiment includes the X-ray tube 6*b* instead of the X-ray tube 6*a*.

As illustrated in FIG. 9, the X-ray tube 6*b* includes the anode 601*b*, the heat insulating material 602*b*, the magnet 603*b*, a slip ring 6041*b*, a slip ring 6042*b*, a trapping mechanism 605*b*, a cathode 606*b*, the first casing 607*b*, a fourth sensor 608*b*, a second casing 609*b*, a floating coil 610*b*, a propulsion coil 611*b*, a propulsion coil 612*b*, an X-ray leakage prevention cover 6131*b*, an X-ray leakage prevention cover 6132*b*, and a deflection electrode 614*b*. Note that the configuration of the X-ray tube 6*b* is not limited to the following configuration.

As illustrated in FIG. 9, the anode 601*b* generates an X-ray R by receiving electrons E emitted from the cathode 606*b*. As illustrated in FIG. 9, the shape of the anode 601*b* is a solid of revolution about the rotation axis Zr. The anode 601*b* receives the electrons E emitted from the cathode 606*b*. As illustrated in FIG. 9, the radius in a portion of the anode 601*b* at which the electrons E are received becomes smaller as the distance to the cathode 606*b* becomes smaller. Furthermore, the anode 601*b* is connected to the first casing 607*b*. Specifically, the anode 601*b* is connected to a side surface of the first casing 607*b* on the +Z direction side.

Furthermore, the anode 601*b* rotates about the rotation axis Zr while floating in the space due to electromagnetic force. Specifically, the anode 601*b* floats in the space together with the first casing 607*b* due to electromagnetic force generated between the floating coil 610*b* and the magnet 603*b*. Furthermore, the anode 601*b* rotates about the rotation axis Zr together with the first casing 607*b* due to electromagnetic force generated between the propulsion coil 611*b* and the magnet 603*b* and electromagnetic force generated between the propulsion coil 612*b* and the magnet 603*b*.

The heat insulating material 602*b* prevents heat generated by the anode 601*b* from being transferred to the magnet 603*b*. As illustrated in FIG. 9, the heat insulating material 602*b* is disposed so as to be faced the anode 601*b* across the side surface of the first casing 607*b* on the +Z direction side.

The magnet 603*b* generates magnetic poles. Specifically, the magnet 603*b* generates a magnetic moment. The magnetic moment generated by the magnet 603*b* is parallel to the rotation axis Zr. The magnet 603*b* is connected to the anode 601*b*. Specifically, as illustrated in FIG. 9, the magnet 603*b* is disposed so as to be faced the side surface of the first casing 607*b* on the +Z direction side across the heat insulating material 602*b*. The magnets 603*b* are disposed so as to surround the rotation axis Zr. The magnets 603*b* orbit on a circular orbit around a point on the rotation axis Zr due to the rotation of the anode 601*b*.

The slip ring 6041*b* electrically connects the anode 601*b* and the cathode 606*b* to each other. The slip ring 6042*b* electrically connects the cathode 606*b* and the anode 601*b* to each other.

The trapping mechanism 605*b* traps the anode 601*b*. Specifically, the trapping mechanism 605*b* traps the anode 601*b* by trapping the first casing 607*b*. In this case, the center of gravity of the whole of the anode 601*b*, the heat insulating material 602*b*, the magnet 603*b*, and the first casing 607*b* is located on the anode 601*b* side. Accordingly, the trapping mechanism 605*b* traps a part, which is closer to the anode 601*b*, of the first casing 607*b* as illustrated in FIG. 9. In this manner, the trapping mechanism 605*b* can stably trap the anode 601*b*.

As illustrated in FIG. 9, the cathode 606*b* emits electrons E. The electrons E emitted by the cathode 606*b* are accelerated by a voltage applied between the anode 601*b* and the cathode 606*b*. Furthermore, as illustrated in FIG. 9, the trajectory of the electrons E emitted by the cathode 606*b* is adjusted by the deflection electrode 614*b*.

As illustrated in FIG. 9, the first casing 607*b* houses therein the anode 601*b* and the cathode 606*b*. For example, the first casing 607*b* is made of glass. Furthermore, the first casing 607*b* includes a first X-ray window 6071*b*. Note that the first casing 607*b* is also referred to as "insert".

The fourth sensor 608*b* detects the position of the anode 601*b* in the X-ray tube 6*b*. Specifically, the fourth sensor 608*b* detects the position of the first casing 607*b* in the X-ray tube 6*b*, thereby detecting the position of the anode 601*b*. As used herein, the positions of the first casing 607*b* and the anode 601*b* in the X-ray tube 6*b* refer to the positions in the X direction, the Y direction, and the Z direction. As illustrated in FIG. 9, a plurality of the fourth sensors 608*b* is mounted to an inner wall of the second casing 609*b*. Detection results of the fourth sensors 608*b* are transmitted to the floating coil control circuitry.

The deflection electrode 614*b* generates an electric field to adjust the trajectory of the electrons E emitted by the cathode 606*b*. In this manner, the electrons E emitted by the cathode 606*b* collide with the anode 601*b* at predetermined positions. Note that the X-ray tube 6*b* may include a deflection coil instead of the deflection electrode 614*b*. The deflection coil generates a magnetic field to adjust the trajectory of the electrons E emitted by the cathode 606*b*.

As illustrated in FIG. 9, the second casing 609*b* houses therein the heat insulating material 602*b*, the magnet 603*b*, the slip ring 6041*b*, the slip ring 6042*b*, the trapping mechanism 605*b*, the first casing 607*b*, the fourth sensor 608*b*, and the deflection electrode 614*b*. Furthermore, the second casing 609*b* includes a second X-ray window 6091*b*. In addition, the second casing 609*b* includes the same number of electromagnetic force windows 6092*b* as the floating coils 610*b*.

As illustrated in FIG. 9, the electromagnetic force window 6092*b* covers the entire coil face of every floating coil 610*b* on the +Z direction side or the −Z direction side. Furthermore, the electromagnetic force window 6092*b* is manufactured by a material that does not block the electromagnetic force generated between the magnet 603*b* and the floating coil 610*b*, the electromagnetic force generated between the magnet 603*b* and the propulsion coil 611*b*, and the electromagnetic force generated between the magnet 603*b* and the propulsion coil 612*b*. Examples of such material include glass and resin.

As illustrated in FIG. 9, the region between the first casing 607*b* and the second casing 609*b* is filled with cooling oil L. The cooling oil L absorbs heat generated by the anode 601*b* through heat conduction. Consequently, the cooling oil L can prevent the heat generated by the anode 601*b* from being transferred to other parts of the X-ray tube 6*b*. Furthermore, the anode 601*b* is cooled through heat conduction and hence the X-ray tube 6*b* can shorten the time for waiting for cooling. The cooling oil L is circulated by a pump connected to the region between the first casing 607*b* and the second casing 609*b*. Consequently, the above-mentioned effect of the cooling oil L is further enhanced.

As illustrated in FIG. 9, the X-ray leakage prevention cover 6131*b* covers the whole of the electromagnetic force windows 6092*b*, the floating coils 610*b*, the propulsion coils 611*b*, and the propulsion coils 612*b* that are installed on a surface of the second casing 609*b* on the −Z direction side. Similarly, the X-ray leakage prevention cover 6132*b* covers the whole of the electromagnetic force windows 6092*b*, the floating coils 610*b*, the propulsion coils 611*b*, and the propulsion coils 612*b* that are installed on a surface of the second casing 609*b* on the +Z direction side. Furthermore, the X-ray leakage prevention cover 6131*b* and the X-ray leakage prevention cover 6132*b* are manufactured by a material that can block an X-ray. Examples of the material that can block an X-ray include lead. Consequently, the X-ray leakage prevention cover 6131*b* and the X-ray leakage prevention cover 6132*b* can prevent an X-ray that is generated by the anode 601*a* and transmits through the electromagnetic force window 6092*b* from leaking to the outside of the X-ray tube 6*b*.

As illustrated in FIG. 9, the floating coil 610*b* is installed between the electromagnetic force window 6092*b* and the propulsion coil 611*b*. As illustrated in FIG. 9, one coil face of the floating coil 610*b* is in contact with the electromagnetic force window 6092*b* that is installed on a side surface of the second casing 609b on the +Z direction side or the −Z direction side. As illustrated in FIG. 9, the other coil face of the floating coil 610b is in contact with one coil face of the propulsion coil 611b. The floating coil 610b is formed by winding a conductive wire into a figure of eight. Furthermore, as illustrated in FIG. 10, the floating coils 610b are disposed so as to surround the rotation axis Zr.

The floating coil control circuitry controls a current to be supplied to the floating coil 610b based on at least one of the position of the X-ray tube 6b, the direction of the X-ray tube 6b, the velocity of the X-ray tube 6b, or the position of the anode 601b in the X-ray tube 6b. Specifically, the floating coil control circuitry controls the current to be supplied to the floating coil 610b based on a detection result of at least one of the first sensor 12, the second sensor 13, the third sensor 14, or the fourth sensor 608b. In this manner, the anode 601b can constantly float in the space. In the second embodiment, however, the anode 601b is connected to the first casing 607b and hence the first casing 607b as well as the anode 601b constantly float in the space.

As illustrated in FIG. 9, the propulsion coil 611b and the propulsion coil 612b are installed between the surface of the second casing 609b on the −Z direction side and the X-ray leakage prevention cover 6131b. As illustrated in FIG. 9, the propulsion coil 611b and the propulsion coil 612b may be installed between the surface of the second casing 609b on the +Z direction side and the X-ray leakage prevention cover 6132b.

As illustrated in FIG. 9, the propulsion coil 611b is disposed so as to be faced the side surface of the second casing 609b on the −Z direction side across the first casing 607b and the floating coil 610b. As illustrated in FIG. 9, the propulsion coil 612b is disposed so as to be faced the side surface of the second casing 609b on the −Z direction side across the floating coil 610b and the propulsion coil 611b. Furthermore, as illustrated in FIG. 10, the propulsion coil 611b and the propulsion coil 612b are disposed so as to surround the rotation axis Zr. A method of rotating the anode 601b about the rotation axis Zr by the propulsion coil 611b and the propulsion coil 612b is the same as that in the first embodiment. In the second embodiment, however, the anode 601b is connected to the first casing 607b and hence the first casing 607b as well as the anode 601b rotate about the rotation axis Zr.

As described above, the X-ray CT apparatus according to the second embodiment includes the X-ray tube 6b. The X-ray tube 6b exhibits the same effects as those of the X-ray tube 6a according to the first embodiment. Furthermore, the X-ray tube 6b cools the anode 601b by the cooling oil L. Consequently, the X-ray tube 6b can suppress an increase in temperature of the anode 601b. Furthermore, the X-ray tube 6b can prevent heat generated by the anode 601b from being transferred to other parts of the X-ray tube 6b. In addition, the X-ray tube 6b can shorten the time for waiting for cooling.

Third Embodiment

In the first embodiment, only the anode 601a, the heat insulating material 602a, and the magnet 603a rotate about the rotation axis Zr. Also in a third embodiment, only an anode 601c, a heat insulating material 602c, and a magnet 603c rotate about the rotation axis Zr similarly to the first embodiment. An X-ray tube 6c according to the third embodiment is now described. Note that the contents overlapping with those in the above-mentioned embodiments are denoted by the same reference symbols and detailed descriptions thereof are omitted.

The first sensor 12 detects the position of the X-ray tube 6c. For example, the first sensor 12 is mounted to the gantry 2. Alternatively, the first sensor 12 is mounted to the X-ray tube 6c. A method of detecting the position of the X-ray tube 6c by the first sensor 12 is not particularly limited.

The second sensor 13 detects the direction of the X-ray tube 6c. For example, the second sensor 13 is mounted to the X-ray tube 6c. A method of detecting the direction of the X-ray tube 6c by the second sensor 13 is not particularly limited.

The third sensor 14 detects the velocity of the X-ray tube 6c. For example, the third sensor 14 is mounted to the gantry 2. Alternatively, the third sensor 14 is mounted to the X-ray tube 6c. A method of detecting the velocity of the X-ray tube 6c by the third sensor 14 is not particularly limited.

Figure 11:
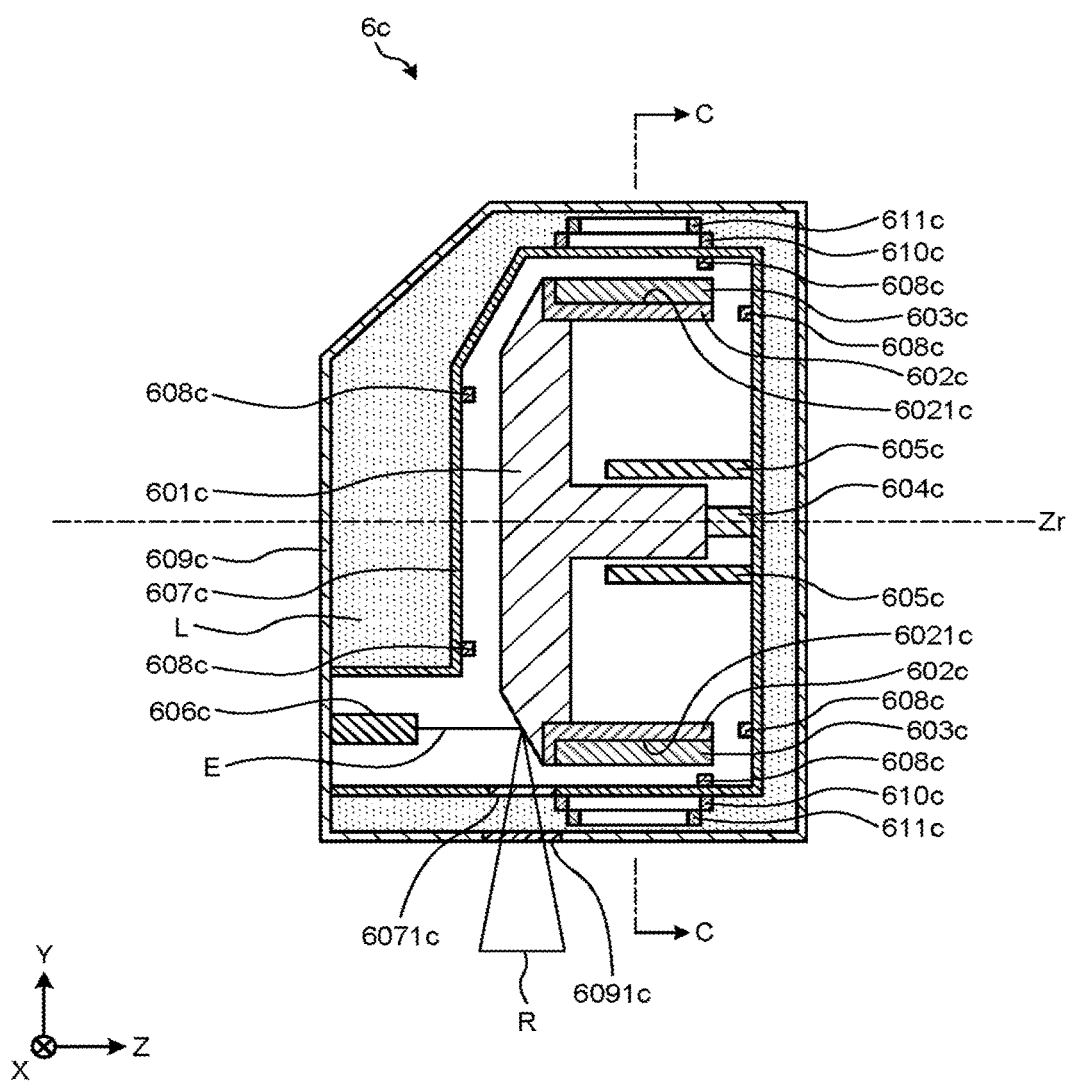
FIG. 11 is a diagram of an X-ray tube according to a third embodiment, which is cut by a plane that passes through a rotation axis Zr and is parallel to the YZ plane, and which is viewed in the −X direction.
Figure 12:
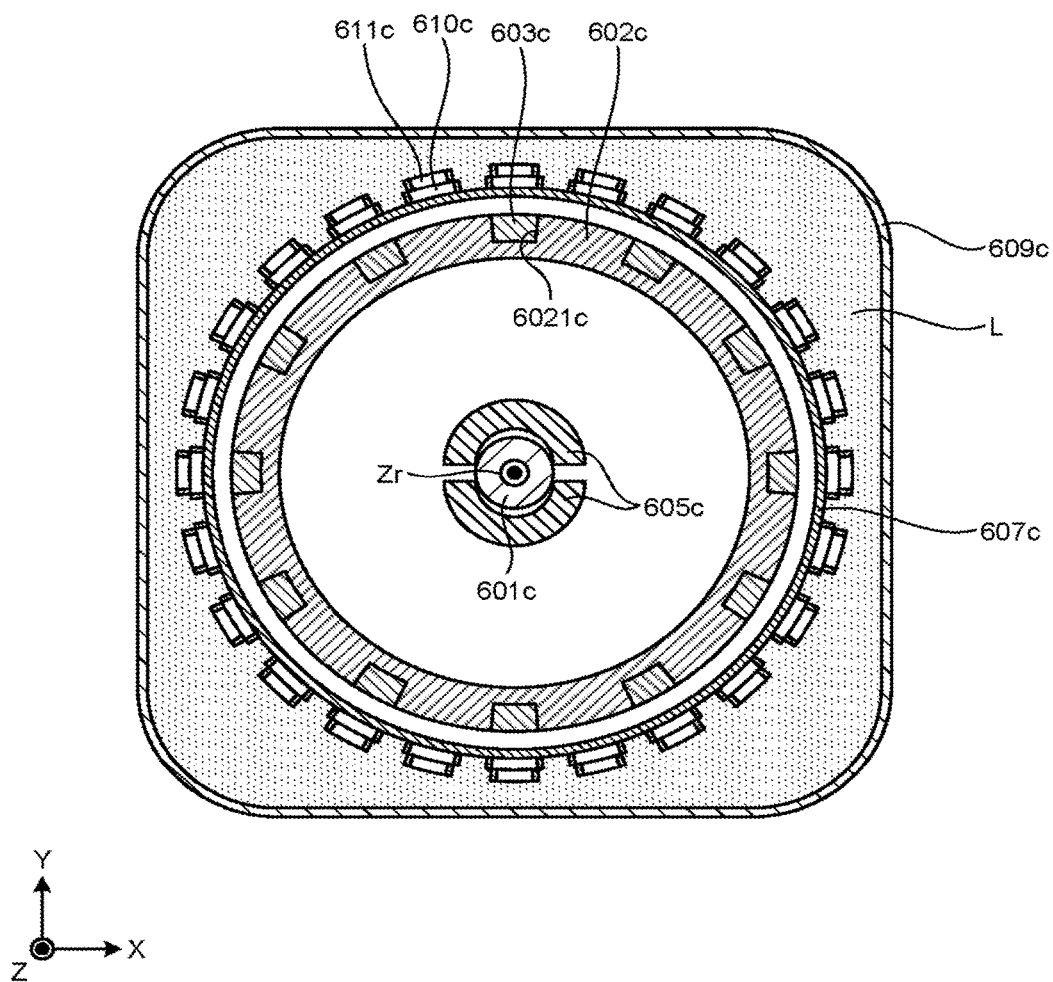
FIG. 12 is a diagram of the X-ray tube according to the third embodiment, which is cut by a plane that passes through the line C-C illustrated in FIG. 11 and is parallel to the XY plane, and which is viewed in the +Z direction.

Referring to FIG. 11 and FIG. 12, the structure and operation of the X-ray tube 6c according to the third embodiment are described. FIG. 11 is a diagram of the X-ray tube according to the third embodiment, which is cut by a plane that passes through the rotation axis Zr and is parallel to the YZ plane, and which is viewed in the −X direction. FIG. 12 is a diagram of the X-ray tube according to the third embodiment, which is cut by a plane that passes through the line C-C illustrated in FIG. 11 and is parallel to the XY plane, and which is viewed in the +Z direction.

As illustrated in FIG. 11, the X-ray tube 6c includes the anode 601c, the heat insulating material 602c, the magnet 603c, a slip ring 604c, a trapping mechanism 605c, a cathode 606c, a first casing 607c, a fourth sensor 608c, a second casing 609c, a floating coil 610c, and a propulsion coil 611c. Note that the configuration of the X-ray tube 6c is not limited to the following configuration.

As illustrated in FIG. 11, the anode 601c generates an X-ray R by receiving electrons E emitted from the cathode 606c. As illustrated in FIG. 11, the shape of the anode 601c is a solid of revolution about the rotation axis Zr. The anode 601c has a large-radius portion and a small-radius portion. The large-radius portion is located on the −Z direction side of the anode 601c. The small-radius portion is located on the +Z direction side of the anode 601c. The anode 601c receives the electrons E emitted from the cathode 606c at the large-radius portion. As illustrated in FIG. 11, the radius in the portion of the anode 601c at which the electrons E are received becomes smaller as the distance to the cathode 606c becomes smaller.

Furthermore, the anode 601c rotates about the rotation axis Zr while floating in the space due to electromagnetic force. Specifically, the anode 601c floats in the space due to electromagnetic force generated between the floating coil 610c and the magnet 603c. Furthermore, the anode 601c rotates about the rotation axis Zr due to electromagnetic force generated between the propulsion coil 611c and the magnet 603c.

The heat insulating material 602c prevents heat generated by the anode 601c from being transferred to the magnet 603c. As illustrated in FIG. 11 and FIG. 12, the shape of the heat insulating material 602c is a cylinder. As illustrated in FIG. 11 and FIG. 12, the heat insulating material 602c has a hole 6021c. The magnet 603c is inserted in the hole 6021c.

The magnet 603c generates magnetic poles. Specifically, the magnet 603c generates a magnetic moment. The magnetic moment generated by the magnet 603c is perpendicular to the rotation axis Zr. The magnet 603c is connected to the anode 601c. Specifically, the magnet 603c is inserted in the hole 6021c of the heat insulating material 602c. As illustrated in FIG. 12, the magnets 603c are disposed so as to surround the rotation axis Zr. The magnets 603c orbit on a circular orbit around a point on the rotation axis Zr due to the rotation of the anode 601c.

The slip ring 604c electrically connects the anode 601c and the cathode 606c to each other.

The trapping mechanism 605c traps the anode 601c. Specifically, the trapping mechanism 605c traps the small-radius portion of the rotating anode 601c, for example, in instantaneous power failure, at the time of power-on of the X-ray tube 6c, or at the time of power-off of the X-ray tube 6c. As illustrated in FIG. 11 and FIG. 12, the trapping mechanism 605c includes two half-cylinders. For trapping the anode 601c, the trapping mechanism 605c closes the two half-cylinders. For releasing the anode 601c, the trapping mechanism 605c opens the two closed half-cylinders. FIG. 11 illustrates the state in which the trapping mechanism 605c releases the anode 601c. Note that the trapping mechanism 605c is preferably structured in a manner it does not hinder the rotation of the anode 601c.

As illustrated in FIG. 11, the cathode 606c emits the electrons E.

As illustrated in FIG. 11, the first casing 607c houses therein the anode 601c, the heat insulating material 602c, the magnet 603c, the slip ring 604c, the trapping mechanism 605c, the cathode 606c, and the fourth sensor 608c. Furthermore, the first casing 607c includes a first X-ray window 6071c.

The fourth sensor 608c detects the position of the anode 601c in the X-ray tube 6c. Specifically, the fourth sensor 608c detects the positions of the anode 601c in the X-ray tube 6c in the X direction, the Y direction, and the Z direction. As illustrated in FIG. 11, a plurality of the fourth sensors 608c is mounted to an inner wall of the first casing 607c.

As illustrated in FIG. 11, the second casing 609c houses therein the first casing 607c, the floating coil 610c, and the propulsion coil 611c. Furthermore, the second casing 609c includes a second X-ray window 6091c.

As illustrated in FIG. 11, the floating coil 610c is installed between the first casing 607c and the second casing 609c. As illustrated in FIG. 11 and FIG. 12, the floating coil 610c is disposed on a side surface of the first casing 607c that is parallel to the rotation axis Zr. Furthermore, as illustrated in FIG. 12, the floating coils 610c are disposed so as to surround the rotation axis Zr. The floating coil 610c is formed by winding a conductive wire into a circle. Alternatively, the floating coil 610c is formed by winding a conductive wire so as to form a simple closed curve.

The floating coil 610c generates magnetic poles when supplied with current. Specifically, the floating coil 610c generates a magnetic moment when supplied with current. The magnetic moment generated by the floating coil 610c is perpendicular to the rotation axis Zr. The reason is that the floating coil 610c is disposed so that the coil face thereof faces the rotation axis Zr as illustrated in FIG. 11 and FIG. 12.

One of the magnetic poles of the magnetic moment generated by the floating coil 610c generates at least one of attraction or repulsion between the floating coil 610c and the magnet 603c. This electromagnetic force causes the anode 601c to float in the space. In other words, the floating coil 610c generates at least one of attraction or repulsion between the floating coil 610c and the magnet 603c as the electromagnetic force for causing the anode 601c to float in the space.

The floating coil control circuitry controls a current to be supplied to the floating coil 610c based on at least one of the position of the X-ray tube 6c, the direction of the X-ray tube 6c, the velocity of the X-ray tube 6c, or the position of the anode 601c in the X-ray tube 6c. Specifically, the floating coil control circuitry controls the current to be supplied to the floating coil 610c based on a detection result of at least one of the first sensor 12, the second sensor 13, the third sensor 14, or the fourth sensor 608c. In this manner, the anode 601c can constantly float in the space.

As illustrated in FIG. 11, the propulsion coil 611c is installed between the first casing 607c and the second casing 609c. As illustrated in FIG. 11, the propulsion coil 611c is disposed so as to be faced a side surface of the first casing 607c that is parallel to the rotation axis Zr across the floating coil 610c. Furthermore, as illustrated in FIG. 12, the propulsion coils 611c are disposed so as to surround the rotation axis Zr. The propulsion coil 611c is formed by winding a conductive wire into a circle. Alternatively, the propulsion coil 611c is formed by winding a conductive wire so as to form a simple closed curve.

The propulsion coil 611c generates magnetic poles when supplied with current. Specifically, the propulsion coil 611c generates a magnetic moment when supplied with current. The magnetic moment generated by the propulsion coil 611c is perpendicular to the rotation axis Zr. The reason is that the propulsion coil 611c is disposed so that the coil face thereof faces the rotation axis Zr as illustrated in FIG. 11 and FIG. 12.

One of the magnetic poles of the magnetic moment generated by the propulsion coil 611c generates at least one of attraction or repulsion between the propulsion coil 611c and the magnet 603c. This electromagnetic force rotates the anode 601c about the rotation axis Zr. In other words, the propulsion coil 611c generates at least one of attraction or repulsion between the propulsion coil 611c and the magnet 603c as the electromagnetic force for rotating the anode 601c about the rotation axis Zr.

As illustrated in FIG. 11, the region between the first casing 607c and the second casing 609c is filled with cooling oil L. The cooling oil L is circulated by a pump connected to the region between the first casing 607c and the second casing 609c.

As described above, the X-ray CT apparatus according to the third embodiment includes the X-ray tube 6c. The X-ray tube 6c causes the anode 601c to float in the space by electromagnetic force. Accordingly, the X-ray tube 6c does not require a bearing whose central axis is the rotation axis Zr and which is disposed between the anode 601c and the first casing 607c. This arrangement reduces the radial dimension of the X-ray tube 6c about the rotation axis Zr. Furthermore, the floating coil 610c and the propulsion coil 611c are disposed so that the coil faces thereof face the rotation axis Zr. This arrangement reduces the dimension of the X-ray tube 6c in the Z direction. The X-ray tube 6c is therefore suited for an X-ray CT apparatus, which is required to be small in radial dimension and in Z-direction dimension. Furthermore, the X-ray tube 6c also exhibits the other effects of the X-ray tube 6a according to the first embodiment.

Fourth Embodiment

In the first embodiment, only the anode 601a, the heat insulating material 602a, and the magnet 603a rotate about the rotation axis Zr. Also in a fourth embodiment, only an anode 601d, a heat insulating material 602d, and a magnet 603*d* rotate about the rotation axis Zr similarly to the first embodiment. An X-ray tube 6*d* according to the fourth embodiment is now described. Note that the contents overlapping with those in the above-mentioned embodiments are denoted by the same reference symbols and detailed descriptions thereof are omitted.

The first sensor 12 detects the position of the X-ray tube 6*d*. For example, the first sensor 12 is mounted to the gantry 2. Alternatively, the first sensor 12 is mounted to the X-ray tube 6*d*. A method of detecting the position of the X-ray tube 6*d* by the first sensor 12 is not particularly limited.

The second sensor 13 detects the direction of the X-ray tube 6*d*. For example, the second sensor 13 is mounted to the X-ray tube 6*d*. A method of detecting the direction of the X-ray tube 6*d* by the second sensor 13 is not particularly limited.

The third sensor 14 detects the velocity of the X-ray tube 6*d*. For example, the third sensor 14 is mounted to the gantry 2. Alternatively, the third sensor 14 is mounted to the X-ray tube 6*d*. A method of detecting the velocity of the X-ray tube 6*d* by the third sensor 14 is not particularly limited.

Figure 13:
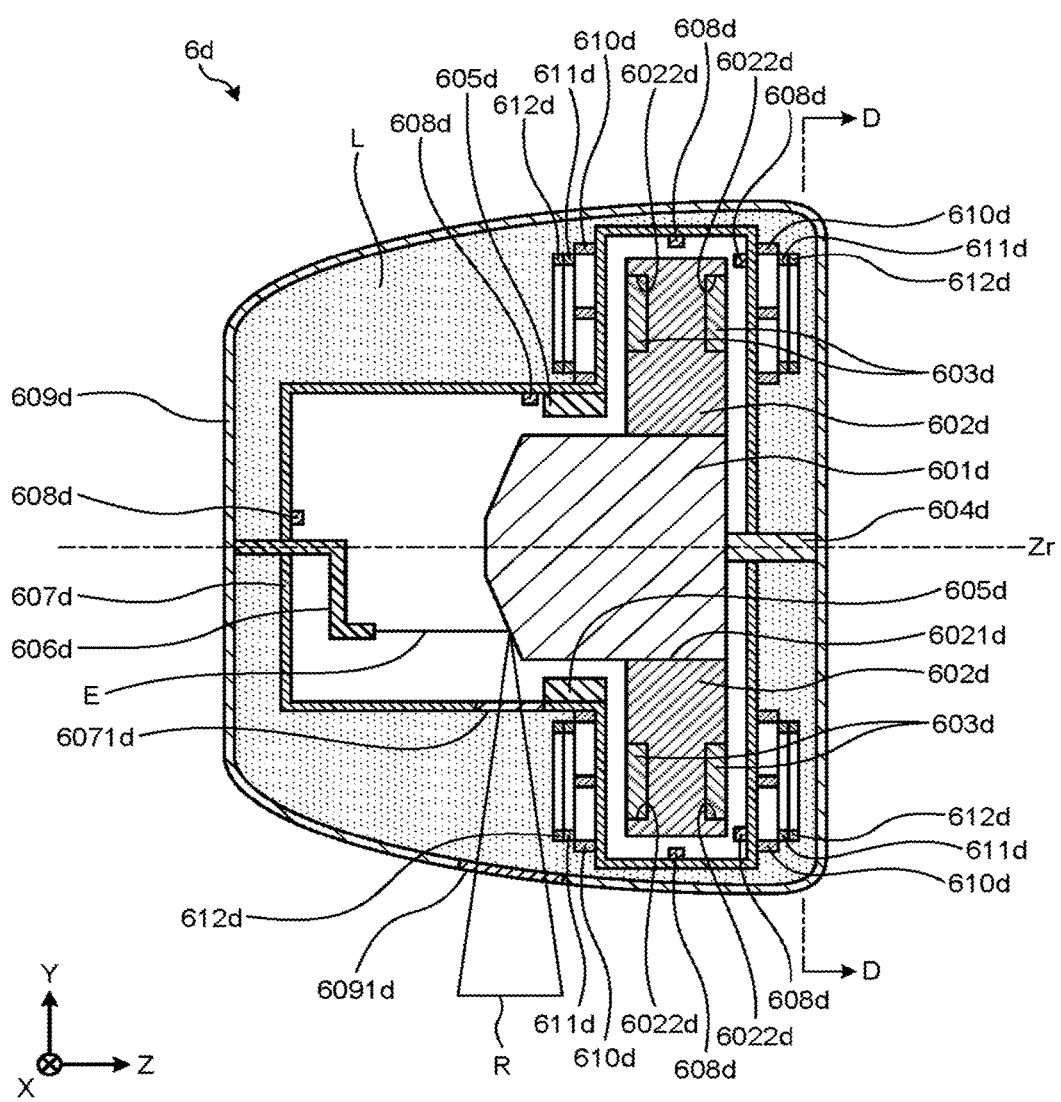
FIG. 13 is a diagram of an X-ray tube according to a fourth embodiment, which is cut by a plane that passes through a rotation axis Zr and is parallel to the YZ plane, and which is viewed in the −X direction.
Figure 14:
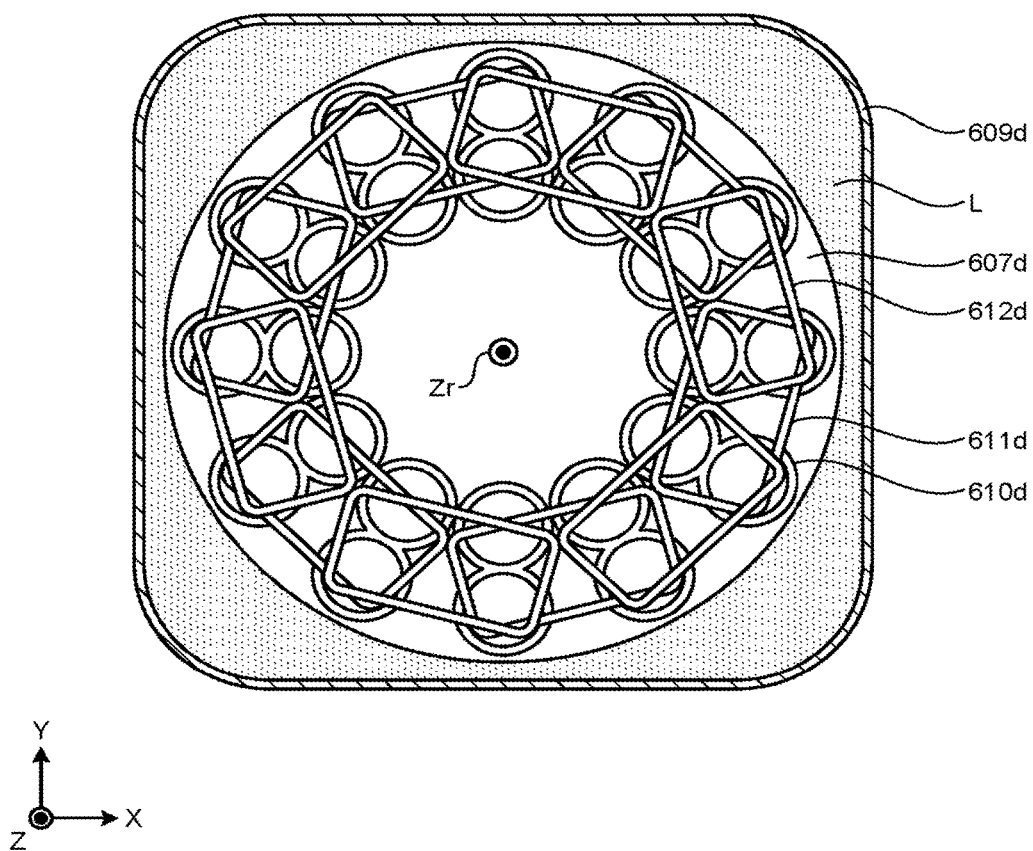
FIG. 14 is a diagram of the X-ray tube according to the fourth embodiment, which is cut by a plane that passes through the line D-D illustrated in FIG. 13 and is parallel to the XY plane, and which is viewed in the +Z direction.

Referring to FIG. 13 and FIG. 14, the structure and operation of the X-ray tube 6*d* according to the fourth embodiment are now described. FIG. 13 is a diagram of the X-ray tube according to the fourth embodiment, which is cut by a plane that passes through the rotation axis Zr and is parallel to the YZ plane, and which is viewed in the −X direction. FIG. 14 is a diagram of the X-ray tube according to the fourth embodiment, which is cut by a plane that passes through the line D-D illustrated in FIG. 13 and is parallel to the XY plane, and which is viewed in the +Z direction.

As illustrated in FIG. 13, the X-ray tube 6*d* includes the anode 601*d*, the heat insulating material 602*d*, a magnet 603*d*, a slip ring 604*d*, a trapping mechanism 605*d*, a cathode 606*d*, a first casing 607*d*, a fourth sensor 608*d*, a second casing 609*d*, a floating coil 610*d*, a propulsion coil 611*d*, and a propulsion coil 612*d*. Note that the configuration of the X-ray tube 6*d* is not limited to the following configuration.

As illustrated in FIG. 13, the anode 601*d* generates an X-ray R by receiving electrons E emitted from the cathode 606*d*. As illustrated in FIG. 13, the shape of the anode 601*d* is a solid of revolution about the rotation axis Zr. The anode 601*d* receives the electrons E emitted from the cathode 606*d*. As illustrated in FIG. 13, the radius in a portion of the anode 601*d* at which the electrons E are received becomes smaller as the distance to the cathode 606*d* becomes smaller.

Furthermore, the anode 601*d* rotates about the rotation axis Zr while floating in the space due to electromagnetic force. Specifically, the anode 601*d* floats in the space due to electromagnetic force generated between the floating coil 610*d* and the magnet 603*d*. Furthermore, the anode 601*d* rotates about the rotation axis Zr due to electromagnetic force generated between the propulsion coil 611*d* and the magnet 603*d* and electromagnetic force generated between the propulsion coil 612*d* and the magnet 603*d*.

The heat insulating material 602*d* prevents heat generated by the anode 601*d* from being transferred to the magnet 603*d*. The shape of the heat insulating material 602*d* is a disc. As illustrated in FIG. 13, the heat insulating material 602*d* has a hole 6021*d* and a hole 6022*d*. Part of the anode 601*d* is inserted in the hole 6021*d*. The magnet 603*d* is inserted in the hole 6022*d*. Note that the heat insulating material 602*d* does not overlap with the anode 601*d* in the Z direction.

The magnet 603*d* generates magnetic poles. Specifically, the magnet 603*d* generates a magnetic moment. The magnetic moment generated by the magnet 603*d* is parallel to the rotation axis Zr. The magnet 603*d* is connected to the anode 601*d*. Specifically, the magnet 603*d* is inserted in the hole 6022*d* of the heat insulating material 602*d*. Furthermore, the magnets 603*d* are disposed separately on the +Z direction side and the −Z direction side. The magnets 603*d* are disposed so as to surround the rotation axis Zr. The magnets 603*d* orbit on a circular orbit around a point on the rotation axis Zr due to the rotation of the anode 601*d*.

The slip ring 604*d* electrically connects the anode 601*d* and the cathode 606*d* to each other. The trapping mechanism 605*d* traps the anode 601*d*. As illustrated in FIG. 13, the cathode 606*d* emits the electrons E.

As illustrated in FIG. 13, the first casing 607*d* houses therein the anode 601*d*, the heat insulating material 602*d*, the magnet 603*d*, the trapping mechanism 605*d*, the cathode 606*d*, and the fourth sensor 608*d*. Furthermore, the first casing 607*d* includes a first X-ray window 6071*d*.

The fourth sensor 608*d* detects the position of the anode 601*d* in the X-ray tube 6*d*.

As illustrated in FIG. 13, the second casing 609*d* houses therein the first casing 607*d*, the floating coil 610*d*, the propulsion coil 611*d*, and the propulsion coil 612*d*. Furthermore, the second casing 609*d* includes a second X-ray window 6091*d*.

As illustrated in FIG. 13, the floating coil 610*d* is installed between the first casing 607*d* and the second casing 609*d*. As illustrated in FIG. 13, the floating coils 610*d* are disposed so as to be faced each other across the first casing 607*d*, the magnet 603*d*, and the heat insulating material 602*d*. The floating coil 610*d* is formed by winding a conductive wire into a figure of eight. Furthermore, as illustrated in FIG. 14, the floating coils 610*d* are disposed so as to surround the rotation axis Zr.

The floating coil control circuitry controls a current to be supplied to the floating coil 610*d* based on at least one of the position of the X-ray tube 6*d*, the direction of the X-ray tube 6*d*, the velocity of the X-ray tube 6*d*, or the position of the anode 601*d* in the X-ray tube 6*d*. Specifically, the floating coil control circuitry controls the current to be supplied to the floating coil 610*d* based on a detection result of at least one of the first sensor 12, the second sensor 13, the third sensor 14, or the fourth sensor 608*d*. In this manner, the anode 601*d* can constantly float in the space.

As illustrated in FIG. 13, the propulsion coil 611*d* and the propulsion coil 612*d* are installed between the first casing 607*d* and the second casing 609*d*. As illustrated in FIG. 13, the propulsion coils 611*d* are disposed so as to be faced each other across the first casing 607*d*, the magnet 603*d*, the heat insulating material 602*d*, and the floating coil 610*d*. As illustrated in FIG. 13, the propulsion coils 612*d* are disposed so as to be faced each other across the first casing 607*d*, the magnet 603*d*, the heat insulating material 602*d*, the floating coil 610*d*, and the propulsion coil 611*d*. Furthermore, as illustrated in FIG. 14, the propulsion coils 611*d* and the propulsion coils 612*d* are disposed so as to surround the rotation axis Zr. As illustrated in FIG. 14, the propulsion coil 611*d* and the propulsion coil 612*d* are each formed by winding a conductive wire into a rectangular shape having four rounded corners.

As illustrated in FIG. 13, the region between the first casing 607*d* and the second casing 609*d* is filled with cooling oil L.

As described above, the X-ray CT apparatus according to the fourth embodiment includes the X-ray tube 6*d*. The X-ray tube 6*d* causes the anode 601*d* to float in the space by electromagnetic force. Accordingly, the X-ray tube 6*d* does not require a bearing whose central axis is the rotation axis Zr and which is disposed between the anode 601*d* and the first casing 607*d*. Furthermore, the floating coil 610*d*, the propulsion coil 611*d*, and the propulsion coil 612*d* are disposed so that the coil faces thereof are orthogonal to the rotation axis Zr. This arrangement reduces the radial dimension of the X-ray tube 6*d* about the rotation axis Zr. Furthermore, the heat insulating material 602*d* does not overlap with the anode 601*d* in the Z direction. This arrangement reduces the dimension of the X-ray tube 6*d* in the Z direction. The X-ray tube 6*d* is therefore suited for an X-ray CT apparatus, which is required to be small in radial dimension and in Z-direction dimension. In addition, the X-ray tube 6*d* can improve the rotational velocity of the anode 601*d* and suppress operational noise. The X-ray tube 6*d* also exhibits the other effects of the X-ray tube 6*a* according to the first embodiment.

The above-mentioned X-ray tube is also applicable to an X-ray diagnostic apparatus. The X-ray CT apparatus 1 is one type of radiographic image diagnostic apparatus. In this case, a C-arm of the X-ray diagnostic apparatus is also referred to as "holding member". The holding member holds the above-mentioned X-ray tube so that the X-ray tube is movable. A mechanism for moving the X-ray tube is optionally employed. Furthermore, the above-mentioned X-ray tube can also be used for applications other than the medical field.

Examples of the above-mentioned processor include a central processing unit (CPU), a graphics processing unit (GPU), an application specific integrated circuit (ASIC), a programmable logic device (PLD), and a field programmable gate array (FPGA). Examples of the programmable logic device (PLD) include a simple programmable logic device (SPLD) and a complex programmable logic device (CPLD).

In the above-mentioned embodiments, the high voltage generation circuitry 3, the collimator adjustment circuitry 4, the gantry drive circuitry 5, the data collection circuitry 10, the coil control circuitry 15, the couch drive circuitry 22, and the processing circuitry 36 implement their functions by reading and executing the computer programs stored in the storage circuitry 35, but the embodiments are not limited thereto. Instead of storing the computer programs in the storage circuitry 35, the computer programs may be directly embedded in the respective items of circuitry. In this case, these items of circuitry implement their functions by reading and executing the computer programs that are directly embedded therein.

The items of circuitry illustrated in FIG. 1 may be dispersed or integrated as appropriate. For example, the processing circuitry 36 may be dispersed in scan control circuitry, pre-processing circuitry, image generation circuitry, display control circuitry, and control circuitry that execute the scan control function 361, the pre-processing function 362, the image generation function 363, the display control function 364, and the control function 365, respectively. Furthermore, for example, the high voltage generation circuitry 3, the collimator adjustment circuitry 4, the gantry drive circuitry 5, the data collection circuitry 10, the floating coil control circuitry, the propulsion coil control circuitry, the couch drive circuitry 22, and the processing circuitry 36 may be integrated as appropriate.

According to at least one of the embodiments described above, the radiographic image diagnostic apparatus that can downsize an X-ray tube and the X-ray tube can be provided.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A radiographic image diagnostic apparatus, comprising:
    an X-ray tube comprising
        a cathode that emits electrons;
        coils that generate electromagnetic force;
        an anode that rotates about a rotation axis in response to the electromagnetic force and generates an X-ray by receiving the electrons; and
        magnets that are connected to the anode and orbit on a circular orbit around a point on the rotation axis due to the rotation of the anode;
    a holding member that holds the X-ray tube so that the X-ray tube is movable; and
    coil control circuitry configured to control a current to be supplied to the coils based on at least one of a position of the X-ray tube, a direction of the X-ray tube, and a velocity of the X-ray tube, wherein
    the coils comprise
        floating coils that generate at least one of attraction or repulsion between the floating coil and the magnets as the electromagnetic force for causing the anode to float in space; and
        propulsion coils that generate at least one of attraction or repulsion between the propulsion coil and the magnets as the electromagnetic force for rotating the anode about the rotation axis.

2. The radiographic image diagnostic apparatus according to claim 1, wherein the coil control circuitry is further configured to control the current to be supplied to the coil based on a position of the anode in the X-ray tube.

3. The radiographic image diagnostic apparatus according to claim 1, wherein the magnets are influenced by the electromagnetic force from both the floating coils and the propulsion coils.

4. The radiographic image diagnostic apparatus according to claim 1, wherein the coil control circuitry is further configured to control a current to be supplied to the floating coils based on at least one of a position of the X-ray tube, a direction of the X-ray tube, a velocity of the X-ray tube, and a position of the anode in the X-ray tube.

5. The radiographic image diagnostic apparatus according to claim 1, further comprising at least one of a first sensor configured to detect a position of the X-ray tube, a second sensor configured to detect a direction of the X-ray tube, and a third sensor configured to detect a velocity of the X-ray tube.

6. The radiographic image diagnostic apparatus according to claim 4, further comprising at least one of a first sensor configured to detect a position of the X-ray tube, a second sensor configured to detect an direction of the X-ray tube, a third sensor configured to detect a velocity of the X-ray tube, and a fourth sensor configured to detect a position of the anode in the X-ray tube.

7. The radiographic image diagnostic apparatus according to claim 1, wherein the magnets, the floating coils, and the propulsion coils each generate magnetic moments parallel to the rotation axis.

8. The radiographic image diagnostic apparatus according to claim 1, wherein each of the floating coils is formed by winding a conductive wire into a figure of eight.

9. The radiographic image diagnostic apparatus according to claim 1, wherein
each of the floating coils comprises a first coil and a second coil that are each formed by winding a conductive wire into a circle, and
a direction of current that flows through the first coil and a direction of current that flows through the second coil are opposite to each other.

10. The radiographic image diagnostic apparatus according to claim 1, wherein the magnets, the floating coils, and the propulsion coils each generate magnetic moments perpendicular to the rotation axis.

11. The radiographic image diagnostic apparatus according to claim 1, further comprising a first casing that houses therein the anode, wherein
the anode is connected to the first casing.

12. The radiographic image diagnostic apparatus according to claim 1, further comprising a trapping mechanism configured to trap the anode.

13. An X-ray tube, comprising:
a cathode that emits electrons;
coils that generate electromagnetic force;
an anode that rotates about a rotation axis in response to the electromagnetic force and generates an X-ray by receiving the electrons; and
magnets that are connected to the anode and orbit on a circular orbit around a point on the rotation axis due to the rotation of the anode; wherein
the coils that rotates the anode being prevented from contacting with the anode, and
the coils comprise
floating coils that generate at least one of attraction or repulsion between the floating coil and the magnets as the electromagnetic force for causing the anode to float in space; and
propulsion coils that generate at least one of attraction or repulsion between the propulsion coil and the magnets as the electromagnetic force for rotating the anode about the rotation axis.

* * * * *

UNITED STATES PATENT AND TRADEMARK OFFICE
CERTIFICATE OF CORRECTION

| | |
|---|---|
| PATENT NO. | : 10,381,188 B2 |
| APPLICATION NO. | : 15/299815 |
| DATED | : August 13, 2019 |
| INVENTOR(S) | : Hiroshi Hirayama |

It is certified that error appears in the above-identified patent and that said Letters Patent is hereby corrected as shown below:

On the Title Page

Item (71), the Applicant name is incorrect. Item (71) should read:
-- (71): Canon Medical Systems Corporation, Otawara-shi (JP) --

Signed and Sealed this
Twenty-ninth Day of October, 2019

Andrei Iancu
*Director of the United States Patent and Trademark Office*